US011369687B2

(12) United States Patent
Medina-Kauwe

(10) Patent No.: US 11,369,687 B2
(45) Date of Patent: Jun. 28, 2022

(54) RECEPTOR TARGETING CONSTRUCTS AND USES THEREOF

(71) Applicant: CEDARS-SINAI MEDICAL CENTER, Los Angeles, CA (US)

(72) Inventor: Lali K. Medina-Kauwe, Porter Ranch, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 189 days.

(21) Appl. No.: 16/197,240

(22) Filed: Nov. 20, 2018

(65) Prior Publication Data

US 2019/0142962 A1 May 16, 2019

Related U.S. Application Data

(62) Division of application No. 15/112,162, filed as application No. PCT/US2015/011870 on Jan. 16, 2015, now Pat. No. 10,183,078.

(60) Provisional application No. 61/928,903, filed on Jan. 17, 2014.

(51) Int. Cl.
| | | |
|---|---|---|
| A61K 47/64 | (2017.01) |
| A61K 31/7105 | (2006.01) |
| C07K 14/005 | (2006.01) |
| A61K 9/00 | (2006.01) |
| A61K 47/68 | (2017.01) |
| A61K 47/69 | (2017.01) |
| A61K 9/51 | (2006.01) |

(52) U.S. Cl.
CPC ............ *A61K 47/64* (2017.08); *A61K 9/0019* (2013.01); *A61K 31/7105* (2013.01); *A61K 47/6803* (2017.08); *A61K 47/6851* (2017.08); *A61K 47/6929* (2017.08); *A61K 9/5169* (2013.01); *C07K 14/005* (2013.01); *C07K 2319/55* (2013.01); *C07K 2319/74* (2013.01)

(58) Field of Classification Search
CPC ................ A61K 47/64; A61K 47/6803; A61K 47/6851; A61K 47/6929; A61K 31/7105
USPC ...................................................... 424/131.1
See application file for complete search history.

(56) References Cited

U.S. PATENT DOCUMENTS

| | | | |
|---|---|---|---|
| 5,391,723 A | 2/1995 | Priest | |
| 5,559,099 A | 9/1996 | Wickham et al. | |
| 6,333,396 B1 | 12/2001 | Filpula et al. | |
| 6,939,963 B2 | 9/2005 | Gross et al. | |
| 8,541,568 B2 | 9/2013 | Yan et al. | |
| 9,078,927 B2 | 7/2015 | Medina-Kauwe | |
| 9,757,386 B2 | 9/2017 | Medina-Kauwe | |
| 9,789,201 B2 | 10/2017 | Medina-Kauwe | |
| 9,850,293 B2 | 12/2017 | Medina-Kauwe | |
| 10,036,099 B2 | 7/2018 | Medina-Kauwe | |
| 10,183,078 B2 | 1/2019 | Medina-Kauwe | |
| 10,793,853 B2 * | 10/2020 | Medina-Kauwe | ...... A61P 35/00 |
| 2003/0138432 A1 | 7/2003 | Glazier | |
| 2003/0170826 A1 | 9/2003 | Rabinovich et al. | |
| 2004/0180872 A1 | 9/2004 | Gross et al. | |
| 2005/0042753 A1 | 2/2005 | Yang et al. | |
| 2005/0048606 A1 | 3/2005 | Wang et al. | |
| 2005/0096502 A1 | 5/2005 | Khalili | |
| 2006/0014712 A1 | 1/2006 | Neuman | |
| 2006/0093674 A1 | 5/2006 | Slobodkin et al. | |
| 2008/0234183 A1 | 9/2008 | Hallbrink et al. | |
| 2011/0052697 A1 | 3/2011 | Farokhzad et al. | |
| 2011/0318338 A1 | 12/2011 | Donald | |
| 2012/0004181 A1 | 1/2012 | Medina-Kauwe | |
| 2012/0071540 A1 | 3/2012 | Lu et al. | |
| 2013/0065778 A1 | 3/2013 | Weidhaas | |
| 2019/0175747 A1 | 6/2019 | Medina-Kauwe | |
| 2019/0240344 A1 | 8/2019 | Haffar | |
| 2021/0077575 A1 | 3/2021 | Medina-kauwe | |
| 2021/0147835 A1 | 5/2021 | Medina-kauwe | |

FOREIGN PATENT DOCUMENTS

| | | | |
|---|---|---|---|
| EP | 1 374 812 A1 | 1/2004 |
| WO | WO-2002/062823 A2 | 8/2002 |
| WO | WO-2002/094318 A1 | 11/2002 |
| WO | WO-2003/045492 A1 | 6/2003 |
| WO | WO-2007/137117 A2 | 11/2007 |
| WO | WO-2009/009441 A2 | 1/2009 |
| WO | WO-2009/009441 A3 | 1/2009 |
| WO | WO-2009/027965 A1 | 3/2009 |
| WO | WO-2010/085665 A2 | 7/2010 |

(Continued)

OTHER PUBLICATIONS

Agadjanian, H. et al. (Feb. 2006). "Specific Delivery of Corroles to Cells via Noncovalent Conjugates with Viral Proteins," *Pharmaceutical Research* 23(2):367-377.

Agadjanian, H. et al. (Apr. 14-18, 2007). "Modified Viral Capsid Protein Mediates Non-Viral Targeting of Unique Non-Covalent Drug Conjugates to HER2+ Breast Cancer Cells," *Proceedings of the AACR Annual Meeting* 48:357, Abstract # 1505, Los Angeles, CA, (Abstract Only), 2 pages.

Agadjanian, H. et al. (Apr. 2008). "Corrole Conjugates: A Unique Approach to Tumor Targeting," *Proceedings of the American Association for Cancer Research Annual Meeting*, 49:549-550. Abstract 2328, Meeting: 99th Annual Meeting of the American-Association-for-Cancer-Research. San Diego, CA, USA. Apr. 12-16, 2008. Amer. Assoc. Canc. Res.

(Continued)

*Primary Examiner* — Yan Xiao
(74) *Attorney, Agent, or Firm* — Morrison & Foerster LLP

(57) ABSTRACT

Disclosed herein are drug delivery molecules that comprise a ligand that targets a cell surface molecule; a membrane penetration domain; and a payload binding domain; and pharmaceutical compositions comprising the same. Also disclosed are methods of treating cancer, inhibiting the progression of cancer, preventing cancer metastasis, and delivering a therapeutic compound to the brain in a subject in need thereof, the methods comprising identifying a subject in need thereof; providing a composition comprising the drug delivery molecule as disclosed herein; and administering an effective amount of the composition to the subject.

10 Claims, 22 Drawing Sheets

Specification includes a Sequence Listing.

(56) References Cited

FOREIGN PATENT DOCUMENTS

| WO | WO-2010/085665 A3 | 7/2010 | | |
|---|---|---|---|---|
| WO | WO-2011/028850 A1 | 3/2011 | | |
| WO | WO 2013151671 | * 10/2013 | ......... | A61K 31/7115 |
| WO | WO-2013/175310 A2 | 11/2013 | | |
| WO | WO-2013/175310 A3 | 11/2013 | | |
| WO | WO-2014/022811 A1 | 2/2014 | | |
| WO | WO-2014/182868 A1 | 11/2014 | | |
| WO | WO-2015/154059 A2 | 10/2015 | | |
| WO | WO-2015/154059 A3 | 10/2015 | | |
| WO | WO-2016/032595 A1 | 3/2016 | | |
| WO | 2019136005 A1 | 7/2019 | | |

OTHER PUBLICATIONS

Agadjanian, H. et al. (Apr. 14, 2009) "Tumor Detection and Elimination by a Targeted Gallium Corrole," *Proc. Nat'l. Acad. Sci. USA* 106(15):6105-6110.

Agadjanian, H. et al. (Mar. 2012). "Chemotherapy Targeting by DNA Capture In Viral Protein Particles," *Nanomedicine* 7(3):335-352, 26 pages.

Albanell, J. et al. (Dec. 1999). "Trastuzumab, A Humanized Anti-HER2 Monoclonal Antibody, For The Treatment Of Breast Cancer," *Drugs Today (Barc)* 35(12):931-946.

Bernstein, H.G. et al. (May 15, 2006, e-pub. Mar. 23, 2006). "Localization Of Neuregulin-1α (Heregulin-α) And One Of Its Receptors, ErbB-4 Tyrosine Kinase, In Developing And Adult Human Brain," *Brain Res. Bull* 69(5):546-559.

Blumenfeld, C.M. et al. (Nov. 2014, e-pub. Jun. 28, 2014). "Cellular Uptake and Cytotoxicity of a Near-IR Fluorescent Corrole-$TiO_2$ Nanoconjugate", *Journal of Inorganic Biochemistry* 140:39-44, 11 pages.

Braslawsky, G.R. et al. (Oct. 15, 1990). "Antitumor Activity of Adriamycin (Hydrazone-linked) Immunoconjugates Compared with Free Adriamycin and Specificity of Tumor Cell Killing," *Cancer Res.* 50:6608-6614.

Candolfi, M. et al. (Sep. 2006, e-pub. Jun. 23, 2006). "Effective High-Capacity Gutless Adenoviral Vectors Mediate Transgene Expression in Human Glioma Cells," *Mol. Ther.* 14(3): 371-381, 22 pages.

Candolfi, M. et al. (Apr. 2006). "Effective Gene Transfer to Human Glioma Cells Using High Capacity Adenoviral Vectors: Human Glioma Cells Express Substantial Levels of CAR and integrin Adenoviral Co-Receptors," *Proceedings of the American Association for Cancer Research Annual Meeting*, 47:70, Abstract 3003, 2 pages.

Chester, K.A. et al. (2000). "Clinical Applications of Phage-Derived sFvs and sFv Fusion Proteins," *Disease Markers* 16(1-2):53-62.

Choudhury, A. et al. (2004). "Small Interfering RNA (siRNA) Inhibits the Expression of the HER2/Neu Gene, Upregulates HLA Class I and Induces Apoptosis of HER2/neu Positive Tumor Cell Lines," *International Journal of Cancer* 108:71-77.

Cobleigh, M.A. et al. (1998). "Efficacy and Safety of Herceptin™ (Humanized Anti-HER2 Antibody) as a Single Agent in 222 Women with HER2 Overexpression Who Relapsed Following Chemotherapy for Metastatic Breast Cancer," Abstract: 376 *Proc. Am. Soc. Clin. Oncol.* 17:97a, 3 pages.

Denny, W.A. (Dec. 1989). "DNA-Intercalating Ligands as Anti-Cancer Drugs: Prospects for Future Design," *Anticancer Drugs Des.* 4(4):241-263.

Drummond, D.C. et al. (1999). "Optimizing Liposomes for Delivery of Chemotherapeutic Agents to Solid Tumors," *Pharmacol. Rev.* 51(4):691-743.

Faltus, T. et al. (Nov./Dec. 2004). "Silencing of the HER2/neu Gene by siRNA Inhibits Proliferation and Induces Apoptosis in HER2/neu-Overexpressing Breast Cancer Cells," *Neoplasia* 6(6):786-795.

Goldman, R. et al. (1990). "Heterodimerization of the erbB-1 and erbB-2 Receptors in Human Breast Carcinoma Cells: A Mechanism for Receptor Transregulation," *Biochemistry* 29(50):11024-11028.

Goren, D. et al. (1996). "Targeting of Stealth Liposomes to erbB-2 (Her/2) Receptor: in Vitro and in Vivo Studies," *Br. J. Cancer* 74:1749-1756.

Hwang, J.Y. et al. (Oct. 10, 2011). "A Mechanistic Study of Tumor-Targeted Corrole Toxicity", *Mol. Pharmaceuticals* 8:2233-2243.

Hwang, J.Y. et al. (Jun. 2011). "Ratiometric Spectral Imaging For Fast Tumor Detection And Chemotherapy Monitoring In Vivo", *Journal of Biomedical Optics* 16(6):066007-1-066007-6.

Hwang, J.Y. et al. (2011) "Multimode Optical Imaging for Translational Chemotherapy: In Vivo tumor Detection and Delineation by Targeted Gallium Corroles", *Proc. of SPIE*. 7902:79020F: 1-8.

Hwang, J.Y. et al. (2011) "Investigating The Photosensitizer-Potential Of Targeted Gallium Corrole Using Multimode Optical Imaging", *Proc. of SPIE*, 7886:78860M:1-6.

Hwang, J.Y. et al. (Jan. 2012, e-pub. Feb. 6, 2012). "Investigating Photoexcitation-Induced Mitochondrial Damage By Chemotherapeutic Corrales Using Multimode Optical Imaging," *Journal of Biomedical Optics* 17(1): 015003-1-015003-11.

Hwang, J.Y. et al. (2012, e-pub. Oct. 4, 2012). "Photoexcitation Of Tumor-Targeted Corroles Induces Singlet Oxygen-Mediated Augmentation Of Cytotoxicity", *Journal of Controlled Release* 163:368-373.

Hwang, J.Y. et al. (2012). "Multimodality Imagining In Vivo for Preclinical Assessment of Tumor-Targeted Doxorubicin Nanoparticles," *PLoS One* 7(4): e34463 (9 pages).

Hwang, J.Y. et al. (Jun. 18, 2013). "Analysis of Targeted Viral Protein Nanoparticles Delivered to HER2+Tumors," *J. Vis. Exp.* 76:50396, 7 pages.

Jeschke, M. et al. (Mar. 3, 1995). "Targeted Inhibition of Tumor-Cell Growth by Recombinant Heregulin-Toxin Fusion Proteins," *Intl. J. Cancer*, 60(5):730-739.

Kanamori, A. et al. (2010). "Neuroprotection Against Superoxide Anion Radical By Metallocorroles In Cellular And Murine Models Of Optic Neuropathy," *J. of Neurochemistry* 114:488-498.

Kedes, L.H. et al. (Aug. 2002). "A Novel Gene Delivery System Targeted to Breast Cancer Cells," Report DAMD17-99-1-9378 prepared for U.S. Army medical research, (38 pages).

Kim, D.-H. et al. (2004, e-pub. Feb. 8, 2004). "Interferon Induction by siRNA' and BsRNAs Synthesized by Phage Polymerase," *Nature Biotechnol.* 22(3):321-325.

Kochut, A. et al. (Jun. 19, 2013). "Bacterial Invasion Factors: Tools for Crossing Biological Barriers and Drug Delivery?" *European Journal of Pharmaceutics and Biopharmaceutics* 84(2):242-250.

Kupershmidt, L. et al. (2010). "Metallocorroles As Cytoprotective Agents Against Oxidative And Nitrative Stress In Cellular Models Of Neurodegeneration," *J. of Neurochemistry* 113:363-373.

Kute, T. et al. (2004), "Development of Herceptin Resistance in Breast Cancer Cells," *Cytometry Part A* 57:86-93.

Mahammed, A. (2005). "Albumin-Conjugated Corrole Metal Complexes: Extremely Simple Yet Very Efficient Biomimetic Oxidation Systems", *J. Am. Chem. Soc.* 127:2883-2887.

Medina-Kauwe, L.K.et al. (Aug. 24-29, 1997). "A Novel Gene Delivery System for Cell-Specific Targeting," *FASEB Journal*, 11(9):A862, Meeting: 17th International Congress of Biochemistry and Molecular Biology in conjunction with the Annual Meeting of the American Society for Biochemistry and Molecular Biology, San Francisco, CA, 1 page.

Medina-Kauwe L.K. et al. (Sep. 2000). "Assessing the Binding and Endocytosis Activity of Cellular Receptors Using GFP-Ligand Fusions," *BioTechniques* 29(3):602-609.

Medina-Kauwe, L.K. et al. (2001). "3PO, a Novel Non-Viral Gene Delivery System Using Engineered Ad5 Penton Proteins," *Gene Therapy* 8:795-803.

Medina-Kauwe, L.K. et al. (Dec. 2001). "Nonviral Gene Delivery to Human Breast Cancer Cells by Targeted Ad5 Penton Proteins," *Gene Therapy* 8(23):1753-1761.

Medina-Kauwe, L.K. (Aug. 2002). "A Novel Gene Delivery System Targeted to Breast Cancer," Report by University of Southern California, Report Sponsored by U.S. Army Medical Research and Material Command, Fort Detrick, Maryland, 14 pages.

Medina-Kauwe, L.K. et al. (Nov. 2002). Ad5 Capsid Protein Uptake and Trafficking in HeLa Cells. *Molecular Biology of the Cell*,

(56) References Cited

OTHER PUBLICATIONS

13(Supplement):541a-542a, Abstract No. 3051, Meeting: 42$^{nd}$ Annual Meeting of the American Society for Cell Biology. San Francisco, CA, USA. American Society for Cell Biology.
Medina-Kauwe, L.K. et al. (2002). "Using GFP-Ligand Fusions to Measure Receptor-Mediated Endocytosis in Living Cells," *Vitamins and Hormones*, 65:81-95.
Medina-Kauwe, L.K. (Nov. 14, 2003). "Endocytosis of Adenovirus and Adenovirus Capsid Proteins," *Adv. Drug Delivery Rev.* 55(11):1485-1496.
Medina-Kauwe, L.K. (2003). "Heregulin-Targeted Protein Uptake for Breast Cancer," NCI: 1R01CA102126-01, Abstract Only, 4 pages.
Medina-Kauwe, L.K. (2004). "Heregulin-Targeted Protein Uptake for Breast Cancer," NCI: 5R01CA102126-02, Abstract Only, 4 pages.
Medina-Kauwe, L.K. (2005). "Heregulin-Targeted Protein Uptake for Breast Cancer," NCI: 5R01CA102126-03, Abstract Only, 4 pages.
Medina-Kauwe, L.K. (2006). "Heregulin-Targeted Protein Uptake for Breast Cancer," NCI: 5R01CA102126-04, Abstract Only, 4 pages.
Medina-Kauwe, L.K. (2005). "Introduction to the Special Issue: Traveling the Intracellular Highway to Gene Therapy," *Gene Therapy* 12:863-864.
Medina-Kauwe, L.K. et al. (2005). "Intracellular Trafficking Of Nonviral Vectors," *Gene Ther*. 12:1734-1751.
Medina-Kauwe, L.K. (2006). "Non-Viral Mediated Gene Delivery for Therapeutic Applications," Chapter 8 in *Gene Therapy for Neurological Disorders*, 115-140.
Medina-Kauwe, L.K. (2007). "A Novel Targeted Therapeutic Using Viral Capsid Protein," NCI: 1R21CA116014-01A2, Abstract Only, 4 pages.
Medina-Kauwe, L.K. (Jun. 2007). "Targeting siRNA Missiles to Her2+ Breast Cancer," retrieved from http://www.dtic.mil/cgi-bin/GetTRDoc?AD=ADA472023, 13 pages.
Medina-Kauwe, L.K. (2008). "A Novel Targeted Therapeutic Using Viral Capsid Protein," NCI: 5R21CA116014-02, Abstract Only, 4 pages.
Medina-Kauwe, L.K. (2008). "Targeting Sima Missiles to Her2+ Breast Cancer", U.S. Army Medical Research and Material Command Fort Detrick, Maryland, 10 pages.
Medina-Kauwe, L.K. (2010). "Protein-DNA Drug Carriers for Tumor Targeting," NCI 5R01CA129822-02, Abstract Only, 5 pages.
Medina-Kauwe, L.K. (2011). "Protein-DNA Drug Carriers for Tumor Targeting," NCI: 4R01CA129822-03, Abstract Only, 5 pages.
Medina-Kauwe, L.K. (2012). "Protein-DNA Drug Carriers for Tumor Targeting," NCI: 5R01CA129822-04, Abstract Only, 5 pages.
Medina-Kauwe, L.K. (2010). "Tumor Targeted Corrales for Detection and Intervention," NCI: 1R01CA140995-01A1, Abstract Only, 5 pages.
Medina-Kauwe, L.K. (2011). "Tumor Targeted Corrales for Detection and Intervention," NCI:5R01CA140995-02, Abstract Only, 5 pages.
Medina-Kauwe, L.K. (2012). "Tumor Targeted Corrales for Detection and Intervention," NCI:5R01CA140995-03, Abstract Only, 5 pages.
Medina-Kauwe, L.K. (2013). "Tumor Targeted Corrales for Detection and Intervention," NCI: 5R01CA140995-04, Abstract Only, 5 pages.
Medina-Kauwe, L.K. (2014). "Tumor Targeted Corrales for Detection and Intervention," NCI: 5R01CA140995-05, Abstract Only, 5 pages.
Medina-Kauwe, (Feb. 2013). "Development Of Adenovirus Capsid Proteins For Targeted Therapeutic Delivery," *Ther. Deliv.* 4(2):267-277, 17 pages.
Minotti, G. et al. (2004). "Anthracyclines: Molecular Advances and Pharmacologic Developments in Antitumor Activity and Cardiotoxicity," *Pharmacol. Rev.* 56(2):185-229.

Pan, D. et al. (2011, e-pub. Jul. 30, 2011) "Manganese-based MRI contrast agents: past, present, and future", *Tetrahedron* 67:8431-8444.
Park, J.W. et al. (2002). "Anti-HER2 Immunoliposomes: Enhanced Efficacy Attributable to Targeted Delivery," *Clin. Cancer Res.* 8:1172-1181.
Project Information for project No. 1R01CA129822-01A2 (2009). Protein-DNA Drug Carriers For Tumor Targeting, Abstract Only, 2 pages.
Project Information for project No. 1R01CA129822-05A1 (2015). Protein-DNA Drug Carriers For Tumor Targeting, Abstract Only, 2 pages.
Rentsendorj, A. et al. (2006; e-published on Feb. 16, 2006). "Typical And Atypical Trafficking Pathways of Ad5 Penton Base Recombinant Protein: Implications for Gene Transfer," *Gene Therapy* 13:821-836.
Ricci, M.S. et al. (Apr. 2006). "Chemotherapeutic Approaches for Targeting Cell Death Pathways," *Oncologist* 11(4):342-357, 26 pages.
Sepp-Lorenzino, L. et al. (Apr. 18, 1996). "Signal Transduction Pathways Induced by Heregulin in MDA-MB-453 Breast Cancer Cells," *Oncogene* 12(8):1679-1687.
Sims, J.D. et al. (Feb. 1, 2013). "Treating Trastuzumab-Resistant HER2+ Breast Cancers with a HER3-Targeted Nanoparticle," *Cancer Research*, 73(3 Supp) Abstract No. A101. Meeting: AACR Special Conference on Tumor Invasion and Metastasis 2013. San Diego, CA, USA Jan. 20, 2013-Jan. 23, 2013 Abstract Only, 2 pages.
Sims J. D. et al. (Dec. 2013). "Abstract P5-08-08: A Human Epidermal Growth Factor Receptor 3 (HER3)-Binding Nanoparticle Targets and Kills Herceptin©-Resistant Human Epidermal Growth Factor Receptor 2 (HER2)-Positive Breast Cancer," *Cancer Research* 73(Suppl. 24) 36$^{th}$ Annual San Antonio Breast Cancer Symposium; San Antonio, TX, USA Dec. 10-14, 2013 Abstract Only.
Sims, J.D. et al. (2015, e-pub. Aug. 31, 2015). "A Corrole Nanobiologic Elicits Tissue-Activated MRI Contrast Enhancement And Tumor-Targeted Toxicity," *J. Control Research* 217:92-101.
Siwak, D.R. et al. (Apr. 2002). "The Potential of Drug-Carrying Immunoliposomes as Anticancer Agents," *Clin. Cancer Res.*, 8:955-956.
Slamon, D.J. et al. (Mar. 15, 2001). Use of Chemotherapy plus a monoclonal antibody against HER2 for metastatic breast cancer that overexpresses HER2, *N. Engl. J. Med.* 344(11):783-792.
Sliwkowski, M.X. et al. (May 20, 1994). "Coexpression of erbB2 and erbB3 proteins Reconstitutes a High Affinity Receptor for Heregulin," *Journal of Biological Chemistry*, 269(20):14661-14665.
Taqavi et al. (Aug. 17, 2008). "Developing Macrocyclic Fluorescent Probes For in Vivo Molecular Imaging," *Abstracts of Papers American Chemical Society*, 236:654-INOR. Meeting: 236$^{th}$ National Meeting of the American-Chemical-Society. Philadelphia, PA, USA. Aug. 17-21, 2008. Amer. Chem. Soc.
Trail, P.A. et al. (Oct. 15, 1992). : "Antigen-Specific Activity of Carcinoma-Reactive BR64-Doxorubicin Conjugates Evaluated in Vitro and in Human Tumor Xenograft Models," *Cancer Res.* 52:5693-5700.
Trail, P.A. et al. (Jul. 9, 1993). "Cure Of Xenografted Human Carcinomas by BR96-Doxorubicin Immunoconjugates," *Science* 261(5118):212-215.
Trail, P.A.et al. (May 2003, e-pub. Jan. 16, 2003). "Monoclonal Antibody Drug Immunoconjugates for Targeted Treatment of Cancer," *Cancer Immunol Immunother*. 52(5):328-337.
Vellinga, J. et al. (2005, e-pub. Mar. 24, 2005). "The Adenovirus Capsid: Major Progress in Minor Proteins," *J. General Virology* 86:1581-1588.
Vogel, C.L. et al. (Feb. 1, 2002). "Efficacy and Safety of Trastuzumab as a Single Agent in First-Line Treatment of HER2-Overexpressing Metastatic Breast Cancer," *J. Clin. Oncol.* 20(3):719-726.
Wolff, A.C. et al. (Nov. 1, 2013, e-pub. Oct. 7, 2013). "Recommendations for Human Epidermal Growth Factor Receptor 2 Testing in Breast Cancer: American Society of Clinical Oncology/College of American Pathologist Clinical Practice Guideline Update," *J. Clin. Oncology* 31(31):3997-4013.

(56) References Cited

OTHER PUBLICATIONS

Xiong, W. et al. (Jan. 2006). "Regulatable Gutless Adenovirus Vectors Sustain Inducible Transgene Expression in the Brain in the Presence of an Immune Response Against Adenoviruses," J. Viro. 80(1):27-37.

Year of Publication retrieved from <http://rep945.infoeach.com/view-OTQ1fDgzNDY1NQ==.html>, last visited on Jun. 21, 2017, 2 pages.

Zabner, J.et al. (Aug. 11, 1995). "Cellular and Molecular Barriers to Gene Transfer by a Cationic Lipid," *Journal of Biological Chemistry* 270(32):18997-19007.

Final Office Acton, dated May 4, 2018, for U.S. Appl. No. 15/112,162, filed Jul. 15, 2016, 15 pages.

Non-Final Office Action, dated Mar. 30, 2017, for U.S. Appl. No. 14/796,758, filed Jul. 10, 2015.

Non-Final Office Acton, dated Oct. 31, 2017, for U.S. Appl. No. 15/112,162, filed Jul. 15, 2016, 22 pages.

Non-Final Office Action, dated Dec. 21, 2018 for U.S. Appl. No. 15/703,323, filed Sep. 13, 2017.

U.S. Appl. No. 13/189,265, filed Jul. 22, 2011, for Medina-Kauwe et al. (Copy not submitted herewith pursuant to the waiver of 37 C.F.R. § 1.98(a)(2)(iii) issued by the Office on Sep. 21, 2004).

U.S. Appl. No. 15/703,323, filed Sep. 13, 2017, for Medina-Kauwe et al. (Copy not submitted herewith pursuant to the waiver of 37 C.F.R. § 1.98(a)(2)(iii) issued by the Office on Sep. 21, 2004).

U.S. Appl. No. 16/017,866, filed Aug. 2, 2013, for Medina-Kauwe et al. (Copy not submitted herewith pursuant to the waiver of 37 C.F.R. § 1.98(a)(2)(iii) issued by the Office on Sep. 21, 2004).

U.S. Appl. No. 15/624,228, filed Jun. 15, 2017, for Medina-Kauwe et al. (Copy not submitted herewith pursuant to the waiver of 37 C.F.R. § 1.98(a)(2)(iii) issued by the Office on Sep. 21, 2004).

U.S. Appl. No. 15/816,881, filed Nov. 17, 2017, for Medina-Kauwe et al. (Copy not submitted herewith pursuant to the waiver of 37 C.F.R. § 1.98(a)(2)(iii) issued by the Office on Sep. 21, 2004).

\* cited by examiner

Synthetic mRNA encoding GFP
- Single-strand
- 1kb
- Translates into GFP

GFP expression

Schematic of PBK10 + mRNA complex

PBK10 + synth mRNA

Cell binding by PBK10-mRNA

FIG. 2E  Cell entry of PBK10-mRNA
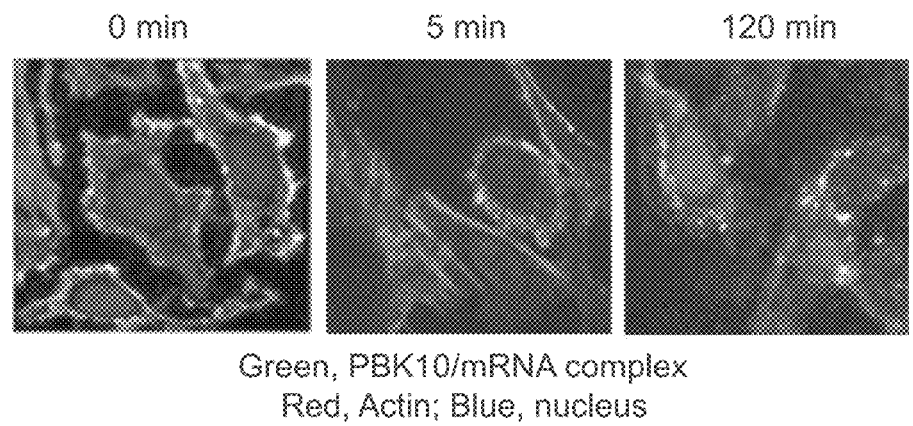
Green, PBK10/mRNA complex
Red, Actin; Blue, nucleus
FIG. 2F  Immunofluorescence of GFP expression
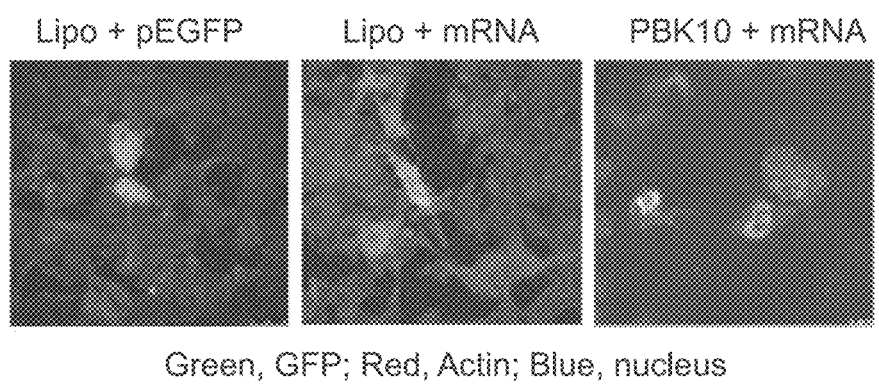
Green, GFP; Red, Actin; Blue, nucleus
FIG. 2G  Optimal PBK10:mRNA ratio
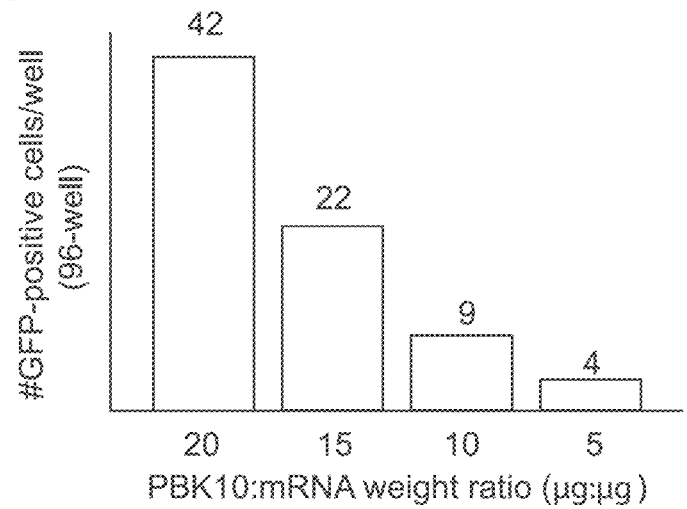

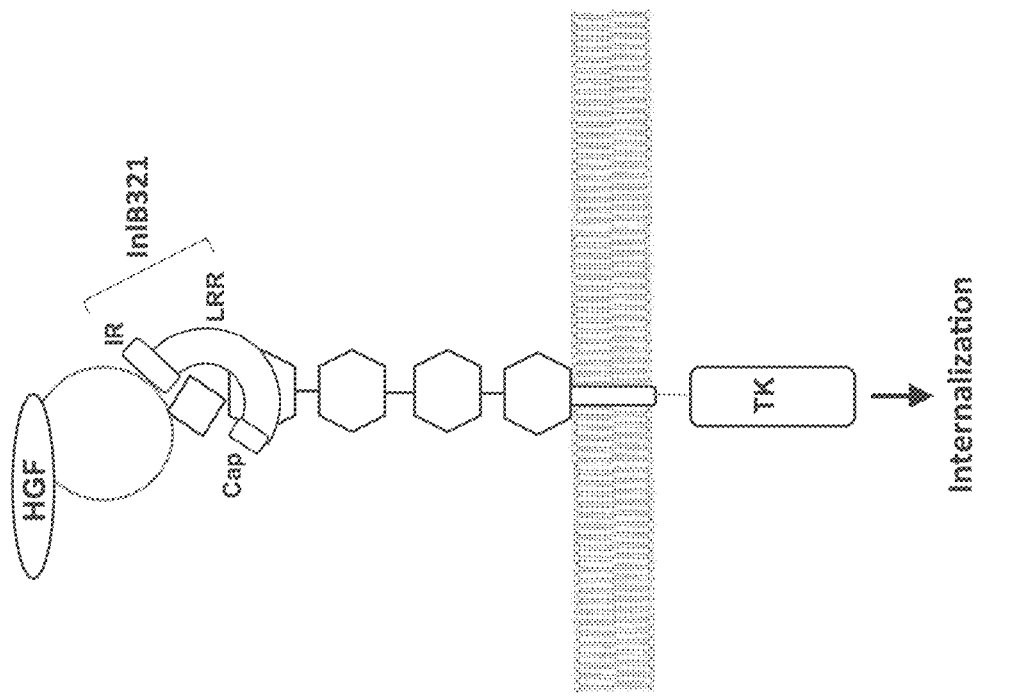
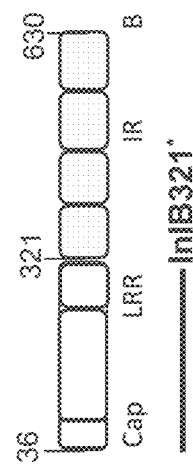
FIG. 3B
FIG. 3A

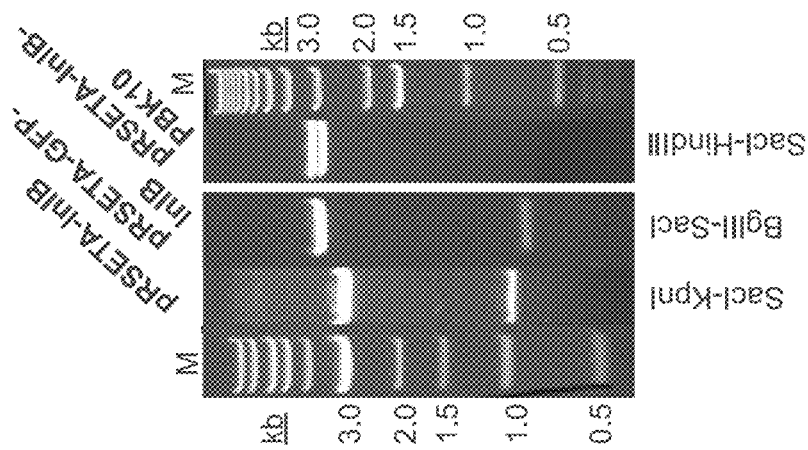
FIG. 4C
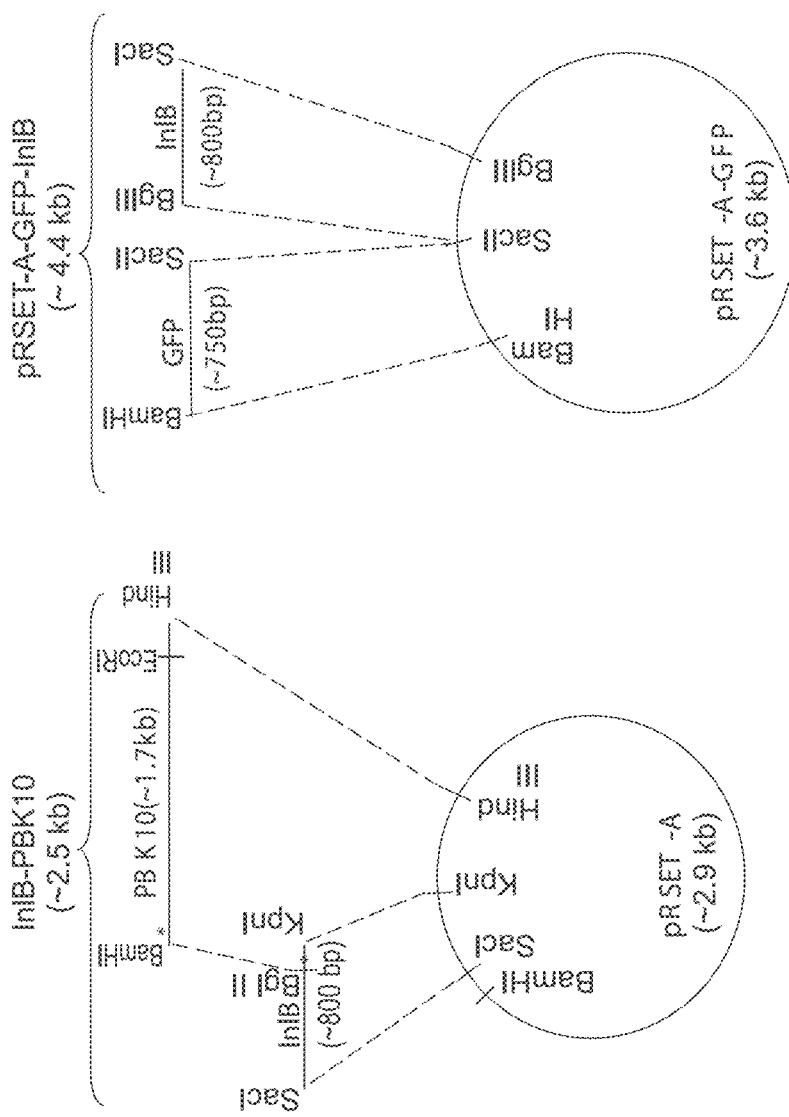
FIG. 4B
FIG. 4A
* Ligating together compatible sites, Bgl II and BamHI, destroys the original sites so that the ligation cannot be recognized by either Bgl II or BamHI for subsequent cleavage.

Lane 1: No Treatment
Lane 2: InlB-PBK10 only
Lane 3: 1:1 InlB-PBK10: InlB
Lane 4: 1:5 InlB-PBK10: InlB
Lane 5: 1:10 InlB-PBK10: InlB

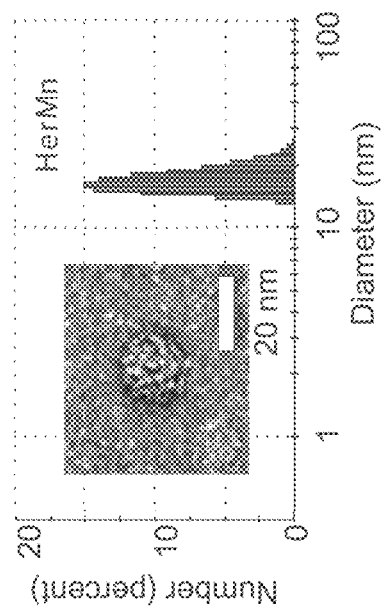
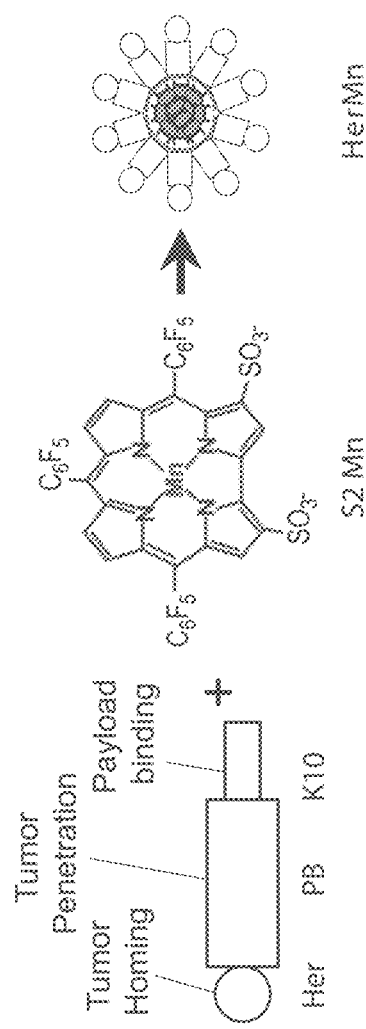
FIG. 11A  FIG. 11B  FIG. 11C  FIG. 11D

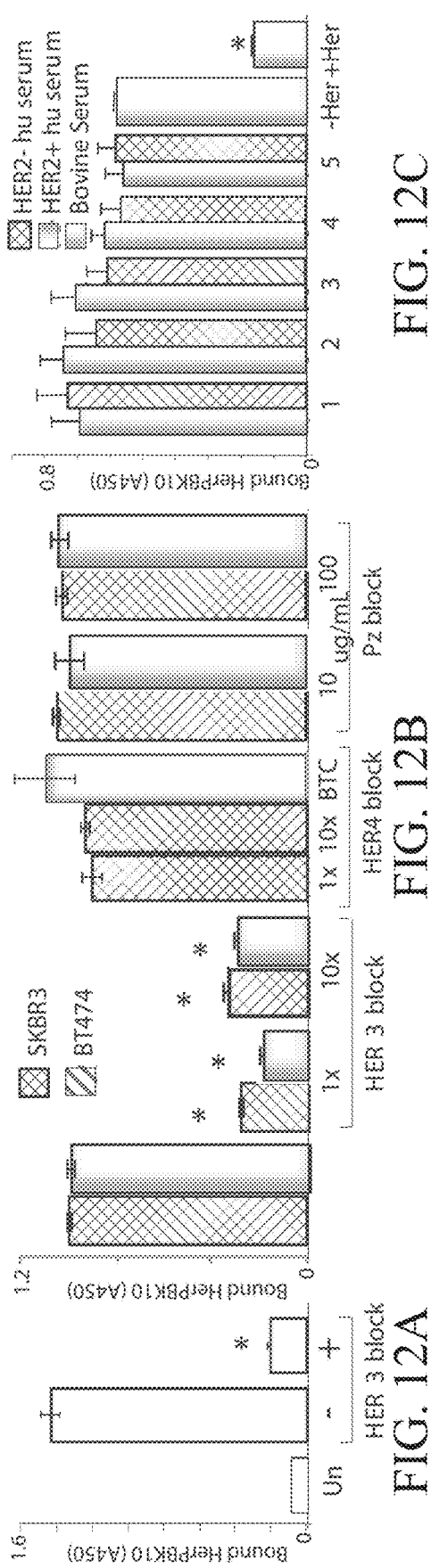
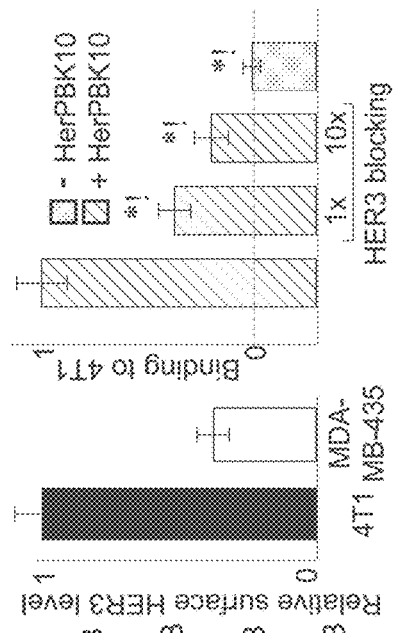
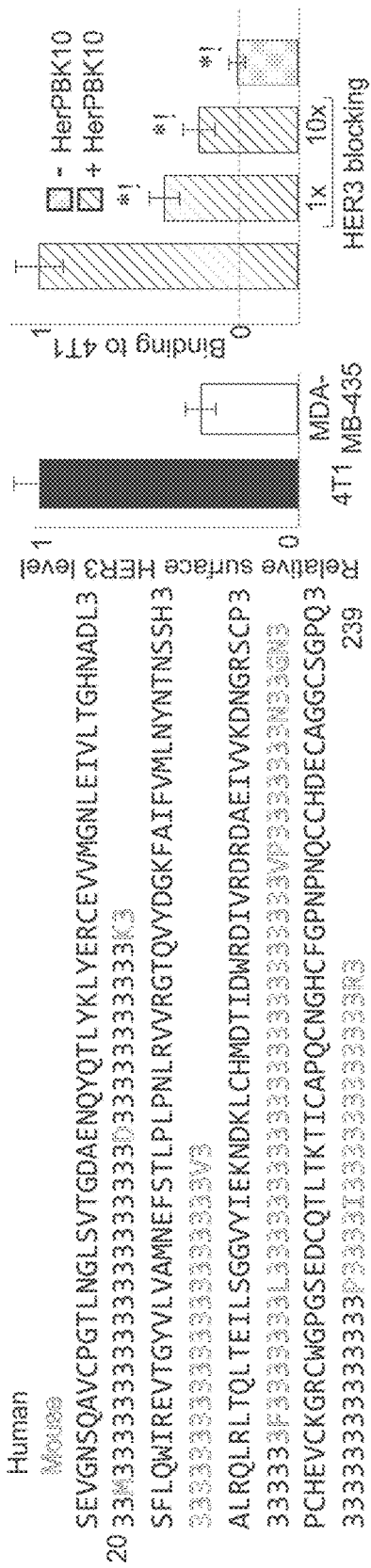
FIG. 12A  FIG. 12B  FIG. 12C
FIG. 13A  FIG. 13B  FIG. 13C

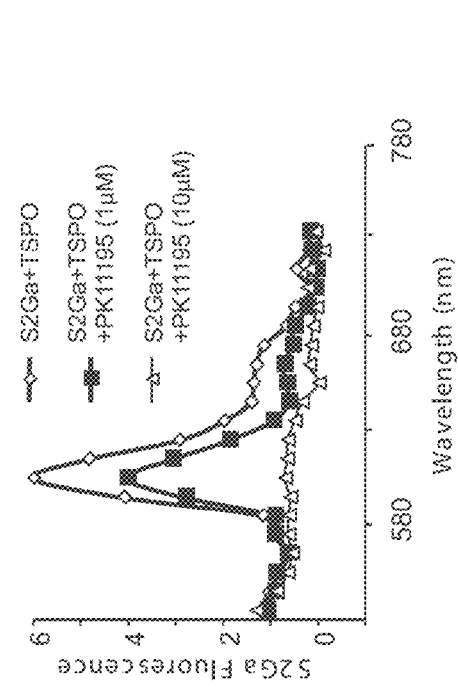
FIG. 16A
FIG. 16B
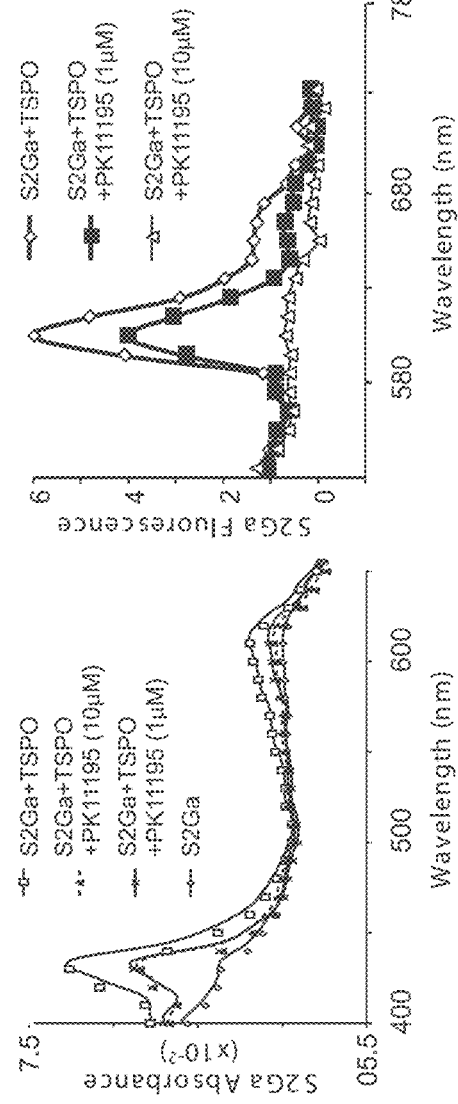
FIG. 16C
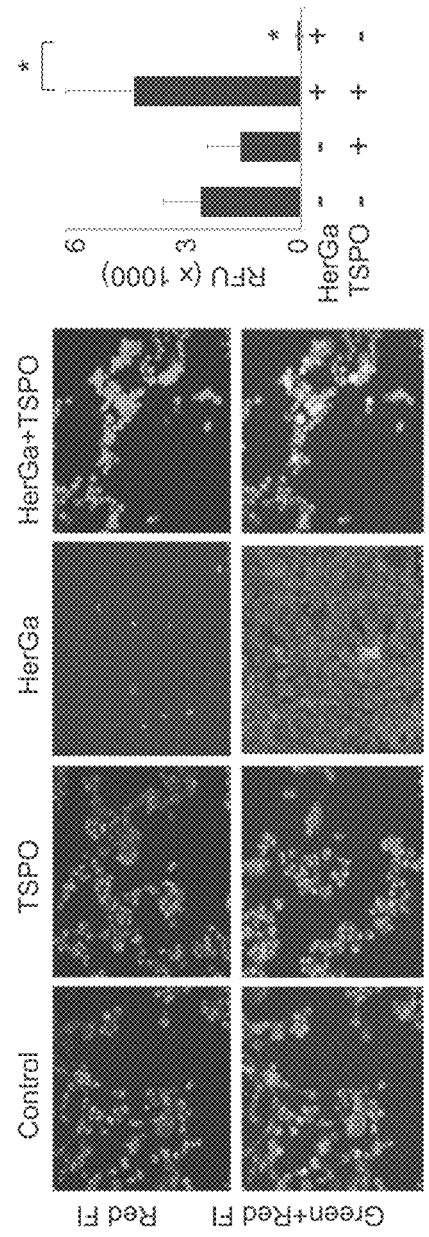
FIG. 16D

RECEPTOR TARGETING CONSTRUCTS AND USES THEREOF

RELATED APPLICATIONS

The present application is a divisional of U.S. patent application Ser. No. 15/112,162, filed on Jul. 15, 2016, entitled "RECEPTOR TARGETING CONSTRUCTS AND USES THEREOF"; which is the U.S. national phase application of International Application No. PCT/US2015/011870, filed on Jan. 16, 2015, entitled "RECEPTOR TARGETING CONSTRUCTS AND USES THEREOF"; which claims priority from U.S. Provisional Application No. 61/928,903, filed on Jan. 17, 2014, entitled "c-MET TARGETING CONSTRUCT AND USES THEREOF," the entire disclosure of each of which is incorporated herein by reference, including the drawings.

GOVERNMENT RIGHTS

This invention was made with government support under Grant No. CA140995 and Grant No. CA129822 awarded by the National Institutes of Health/National Cancer Institute. The government has certain rights in the invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name 203782001110SUBSEQLIST.TXT, date recorded: Jun. 4, 2021, size: 5 KB).

FIELD OF THE INVENTION

The invention relates to the field of biotechnology. Specifically, the invention relates to compositions that deliver therapeutic agents to target cells, such as cancer cells.

BACKGROUND OF THE DISCLOSURE

Many tumors that resist or acquire resistance to current targeted therapies used in the clinic exhibit elevated surface levels of proteins such as c-Met. For example, lung cancer acquires resistance to EGF-R inhibitors such as Tarceva. Inhibitors like Tarceva are intended to block the activity of receptor tyrosine kinases (known as tyrosine kinase inhibitors, or TKI's), but the majority of cases do not respond to TK inhibition. These tumors are characterized by elevated levels of cell surface proteins (such as c-Met) and thus become excellent candidates for therapeutic approaches described herein which approaches can target the overexpressed proteins and penetrate tumor cells.

Current attempts are being made in the field to develop c-Met antibodies or inhibitors that are intended to block signaling through c-Met. However, past history indicates that the majority of cases will not respond to signal blocking antibodies or small molecules because the tumor adopts alternative means to continue proliferating despite signal inhibition.

The compositions described herein circumvent the need to block signaling by using a cell surface receptor (for example, c-Met) as a portal to deliver toxic molecules into the tumor cell and kill tumors from within. Ligand directed delivery enables the targeted binding to tumors that are positive for specific cell surface receptors (for example, c-Met) and the membrane penetration domain in the delivery molecule enables penetration and lysis across the endosomal membrane after cell surface receptor-mediated endocytosis. The delivery protein is also modified to non-covalently assemble with and transport certain therapeutic molecules through, for example, ionic interactions.

SUMMARY OF THE INVENTION

Disclosed herein are drug delivery molecules that comprise a ligand that targets a cell surface molecule; a membrane penetration domain; and a payload binding domain; and pharmaceutical compositions comprising the same. Also disclosed are methods of treating cancer, inhibiting the progression of cancer, preventing cancer metastasis, and delivering a therapeutic compound to the brain in a subject in need thereof, the methods comprising identifying a subject in need thereof; providing a composition comprising the drug delivery molecule as disclosed herein; and administering an effective amount of the composition to the subject.

BRIEF DESCRIPTION OF THE DRAWINGS

FIGS. 2A-2G show that PBK10 can deliver a synthetic mRNA encoding GFP. FIG. 2A provides a summary of mRNA used in this experiment. FIG. 2B shows GFP expression from mRNA delivered by Lipofectin (right) in comparison a GFP-expressing plasmid delivered by Lipofectin (left). FIG. 2C is a schematic of PBK10-mRNA complexes. FIG. 2D shows the cell binding data for PBK10-mRNA complexes. FIG. 2E shows the results of the uptake of cell-bound complexes. FIG. 2F shows the image of the results of the expression of GFP, whereas FIG. 2G depicts the same data in a graph form.

FIGS. 3A-3B are schematics of (FIG. 3A) InlB321, which encompasses the minimal domain for c-MET receptor binding; and (FIG. 3B) InlB321 bound to the extracellular domain of c-MET.

FIGS. 4A-4C are a schematic showing a recombinant gene construct is assembled to encode a new fusion protein, InlB-PBK10. FIG. 4A shows construction of pRSET-InlB-PBK10. FIG. 4B shows construction of pRSET-GFP-InlB. FIG. 4C shows confirmation of cloning inserts by restriction digest.

FIG. 7A shows InlB321 peptide shows preferential binding to c-MET positive, but not low c-MET, cells. Fluorescence activated cell sorting (FACS) was used to measure the relative level of InlB (recognized by immunofluorescence) bound to c-MET positive cells. The FACS data shows a relatively higher level of InlB binding to high c-MET cells (H1993) compared to low c-MET cells (LN GFP). FIG. 7B shows confirmation of c-MET binding by competitive inhibition. InlB binding to H1993 could be inhibited when free InlB was pre-incubated with a soluble peptide derived from the extracellular, ligand binding domain of c-MET (MET) before binding to the cells. InlB and MET were incubated at a 1:1 molar ratio (MET:InlB), which predicts a 50% reduction in receptor binding if InlB is specific to MET. FIG. 7C shows cell binding by InlB-PBK10 is proportional to c-MET levels. InlB-PBK10 showed a higher level of binding to the cells with higher c-MET cell surface expression (MDA-MB-231) in comparison to cells expressing relatively low c-MET levels (Cos-7) as measured by cell surface ELISA. FIG. 7D shows inhibition of binding to c-MET+ cells by competing ligand. Escalating concentrations of free InlB ligand was pre-bound to MDA-MB-231 cells for 1 h on ice before addition of InlB-PBK10 when increasing concentrations of InlB were pre-bound to the cells. FIG. 7E shows InlB-PBK10 undergoes receptor-specific binding to c-MET+ cells in suspension. MDA-MB-435 cells in suspension were incubated with increasing concentrations of free InlB ligand and after removing unbound InlB, cells were incubated with InlB-PBK10. The concentrations of free InlB ligand were chosen so that the molar ratios of InlB-PBK10 to InlB were: 1:1, 1:5, and 1:10. Western blotting was performed to measure the relative InlB-PBK10 levels co-precipitating with the cell pellets. Densitometric measurements (right panel) of immunoblot bands show that levels of InlB-PBK10 binding decreased as the concentration of InlB increased, consistent with InlB-PBK10 binding to c-MET.

FIG. 9A shows preparation of InlB-PBK10-Ga particles. Schematic shows procedure of isolating particles by ultrafiltration after mixing InlB-PBK10 with Ga-corrole to promote non-covalent assembly. FIG. 9B shows DLS of InlB-PBK10-Ga particles. FIG. 9C shows InlB-PBK10 mediates cytosolic entry of the corrole payload.

FIG. 9D shows I-Dox reduces survival of c-MET positive tumor cells. FIG. 9E shows free InlB Inhibits I-Dox toxicity.

FIG. 10A shows images of the whole mouse at indicated time points after tail vein injection. Blue arrows point to kidneys. White arrows point to tumors. FIG. 10B shows images of the tumors and tissues harvested from the same mouse sacrificed after the 4 h time point.

FIGS. 11A-11D depict the assembly of HerMn. FIG. 11A shows a schematic of HerPBK10 protein, highlighting functional domains. FIG. 11B shows the chemical structure of Mn-corrole (S2Mn). FIG. 11C shows a schematic of non-covalent assembly. FIG. 11D shows TEM (inset) and dynamic light scattering (DSL) measurement of HerMn particles in solution.

FIGS. 12A-12C is a group of graphs showing HerPBK10 binds to HER3 and is not inhibited by patient serum. FIG. 12A shows ELISA of HerPBK10 binding to immobilized HER3 (human ErbB3 extracellular domain; Prospec) −/+ pre-incubation with soluble HER3 peptide as a competitive inhibitor (HER3 block). Un: no HerPBK10. FIG. 12B shows ELISA of HerPBK10 binding to HER2+ cells −/+ pre-incubation with: a 1× and 10× molar ratio of soluble HER3 peptide, soluble HER4 peptide (ERBB4 peptide, Abnova), betacellulin (10 μg/mL), or pertuzumab (Pz) as competitive inhibitors. FIG. 12C shows ELISA of HerPBK10 binding to HER2+(MDA-MB-435) cells in serum from five HER2+ patients and age matched controls (HER2−). Control samples were bound in bovine serum and receptor-binding verified by competitive inhibition with recombinant heregulin ligand (+Her). N=3. *, p<0.05 compared to control (−Her: no competitive inhibitor).

FIGS. 13A-13C show the results that HerPBK10 binds to mouse HER3. FIG. 13A shows amino acid sequence alignment of domains I-II (aa 20-239, heregulin-binding domain) of human HER 3 (SEQ ID NO: 14) and mouse HER3. Blue residues indicate amino acid differences. FIG. 13B shows relative HER3 levels detected by ELISA (without permeabilization) using an anti-HER3 antibody that cross-reacts with both human and mouse HER3 (1B2E; Cell Signaling Technologies). FIG. 13C shows binding of HerPBK10 to 4T1 mouse mammary tumor cells. N=3. *, p<0.05 compared to Her PBK10 alone.

FIG. 15A shows confocal fluorescence images showing reduction of mitochondrial membrane potential by HerMn in MDA-MB-435 cells. FIG. 15B shows confocal fluorescence images showing superoxide-mediated collapse of actin (red) and tubulin (green) by HerMn.

FIGS. 16A-16D shows the data that S2Ga interacts with TSPO. FIG. 16A and FIG. 16B show retentates were evaluated for the presence of TSPO-bound corrole by measuring the absorbance and fluorescence spectra. FIG. 16C and FIG. 16D show evidence of HerGa interaction with TSPO in situ. The green fluorescent JC-1 dye used in C fluoresces red when accumulated into mitochondria. FIG. 16D is a quantification of red fluorescence in FIG. 16C. *, p<0.05.

FIG. 18A shows HER2+ MDA-MB-435 tumor growth in female nude mice receiving daily IV (via tail vein) injections of HerMn or S2Mn (5 nmoles corrole/injection) once/day for 6 consecutive days. Control groups received saline or HerPBK10 at equivalent conc to HerMn. Treatments began at ~200 mm³ ave tumor vol. Tumor volumes were measured before (day 1), during (day 3), and after (days 8, 15, and 22) injections of reagents. N=8-10 tumors/group. *p<0.05 (one-way ANOVA). FIG. 18B shows human CDC viability during exposure to HerMn, S2Mn, HerPBK10, or doxorubicin (Dox) for 2 days (solid lines) or 5 days (dashed lines). N=3 per conc, from three separate experiments

DETAILED DESCRIPTION OF THE EMBODIMENTS

Definitions

Figures 1A, 1B:
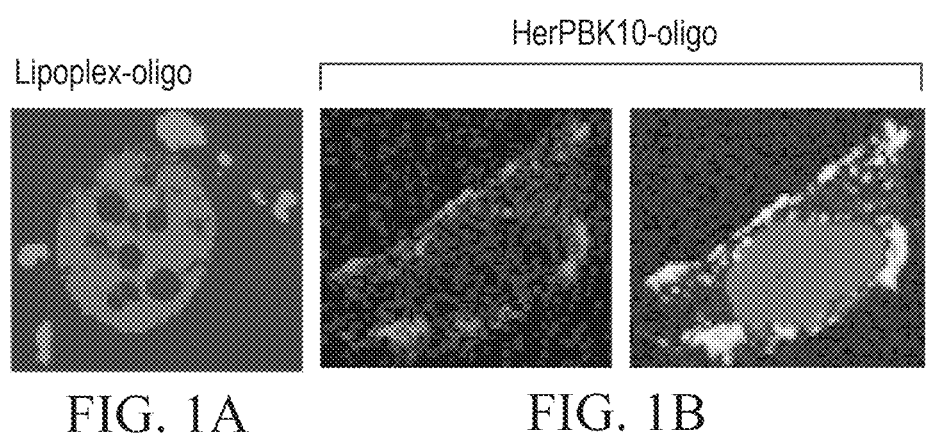
FIGS. 1A-1B show the results of the uptake of a single-stranded oligonucleotide using Lipofectamine as control (FIG. 1A) and HerPBK10 (FIG. 1B).

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. In some embodiments, the disease condition is cancer. In some embodiments, the disease condition is an autoimmune disease.

"Cancer" and "cancerous" refer to or describe the physiological condition in mammals that is typically characterized by unregulated cell growth. Examples of cancer include, but are not limited to leukemia, myeloma, B-cell lymphomas (Hodgkin's lymphomas and/or non-Hodgkins lymphomas), brain cancer, breast cancer, colorectal cancer, lung cancer, hepatocellular cancer, kidney cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, prostate cancer, androgen-dependent prostate cancer, and androgen-independent prostate cancer.

"Chemotherapeutic drugs" or "chemotherapeutic agents" as used herein refer to drugs used to treat cancer including but not limited to Albumin-bound paclitaxel (nab-paclitaxel), Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, or a combination thereof.

"Subject" or "individual" or "animal" or "patient" or "mammal," is meant any subject, particularly a mammalian subject, for whom diagnosis, prognosis, or therapy is desired. In some embodiments, the subject has cancer. In some embodiments, the subject had cancer at some point in the subject's lifetime. In various embodiments, the subject's cancer is in remission, is re-current or is non-recurrent.

"Mammal" as used herein refers to any member of the class Mammalia, including, without limitation, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject. The term does not denote a particular age or sex. Thus, adult and newborn subjects, as well as fetuses, whether male or female, are intended to be included within the scope of this term.

"Treatment," "treating," "therapy," or "therapeutic," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented. A particular procedure or administration is considered therapeutic even if, following the administration, the subject does not feel better. Thus, any amelioration of the subject's disease state, or any slowing of the progression of the disease, is considered therapeutic. Examples of cancer treatment include, but are not limited to, active surveillance, observation, surgical intervention, chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or a combination thereof.

"Tumor," as used herein refers to all neoplastic cell growth and proliferation, whether malignant or benign, and all pre-cancerous and cancerous cells and tissues.

"Therapeutic agents" as used herein refers to agents that are used to, for example, treat, inhibit, prevent, mitigate the effects of, reduce the severity of, reduce the likelihood of developing, slow the progression of and/or cure, a disease. Diseases targeted by the therapeutic agents include but are not limited to carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases.

By "about" a value in the context of the present disclosure it is meant that the disclosure encompasses the listed value ±25%, or alternatively the listed value ±15%, or alternatively the listed value ±10%, or alternatively the listed value ±5%. Thus, for example, by "about 50 amino acids" it is meant 50±25% amino acids (i.e., a range of 37-63 amino acids), or alternatively 50±15% amino acids (i.e., a range of 42-58 amino acids), or alternatively 50±10% amino acids (i.e., a range of 45-55 amino acids), or alternatively 50±5% amino acids (i.e., a range of 47-53 amino acids).

Drug Delivery Molecules

Described herein are drug delivery molecules. The drug delivery molecule includes a ligand that targets a cell surface molecule, a membrane penetration domain and a payload binding domain. The ligand in the drug delivery molecule delivers the molecule to the target cell, such as a cancer cell. The membrane penetration domain mediates cytosolic penetration of the target cell. The payload binding domain forms a complex with a therapeutic agent. The drug delivery molecule in complex with the therapeutic molecule delivers the therapeutic agent to the target cell, such as a cancer cell. In various embodiments, the cancer cell is any one or more of leukemia, myeloma, B-cell lymphomas (Hodgkin's lymphomas and/or non-Hodgkins lymphomas), brain cancer, breast cancer, colorectal cancer, lung cancer, hepatocellular cancer, kidney cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, prostate cancer, androgen-dependent prostate cancer, and androgen-independent prostate cancer.

In some embodiments, the drug delivery molecules disclosed herewith form nanoparticles having between about 5 nm to about 50 nm in diameter. In some embodiments, the nanoparticles have a size of between about 10 to about 30 nm. The payload, i.e., the therapeutic agent, is then bound to the nanoparticle. In one embodiment, the nanoparticle comprises a metallated corrole, for example manganese (Mn), iron (Fe), or gallium (Ga) corrole. In other embodiments, the nanoparticle comprises a protein or a protein fragment. In some embodiments, the binding of the therapeutic agent to the nanoparticle is through a process selected from the group consisting of electrostatic interactions, hydrophobic interactions, hydrophilic interactions, hydrogen bonding, and covalent bonding. Once the nanoparticle-therapeutic agent combination enters a cell, the bond between the nanoparticle and the therapeutic agent is broken, either due to the conditions within the cell that disrupt the association of the nanoparticle and the therapeutic agent, or because the covalent bond between the two is hydrolyzed by an enzyme.

In some embodiments, the cell surface molecule is a receptor that is implicated in a signal transduction pathway that leads to reduced or eliminated apoptosis. Examples of cell surface molecules that may be targeted by a ligand in the drug delivery molecule described herein include, but are not limited to, any one or more of 4-1BB, 5T4, adenocarcinoma antigen, alpha-fetoprotein, BAFF, B-lymphoma cell, C242 antigen, CA-125, carbonic anhydrase 9 (CA-IX), c-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNTO888, CTLA-4, DR5, EGFR, EpCAM, CD3, FAP, fibronectin extra domain-B, folate receptor 1, GD2, GD3 ganglioside, glycoprotein 75, GPNMB, HER2/neu, hepatocyte growth factor (HGF), human scatter factor receptor kinase, IGF-1 receptor, IGF-I, IgG1, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, vimentin or combinations thereof. Other target molecules or particles specific for cancer will be apparent to those of skill in the art and may be used in connection with alternate embodiments of the invention. In an embodiment, the ligand targets c-MET on cancer cells. In an embodiment, the ligand is HGF. In an embodiment, the ligand is Internalin B or a fragment thereof or a variant thereof. In another embodiment, the ligand is the bacterial invasin (Inv) protein.

Thus, in some embodiments, the ligand is a natural binding partner, or a molecule that can bind to the cell surface molecule. In some embodiments, the ligand is a protein, protein fragment, polypeptide, or oligopeptide. In other embodiments, the ligand is an antibody or an antibody fragment. In certain embodiments, the ligand is a small organic molecule that binds to the cell surface molecule. In some embodiments, the small organic molecule mimics the structure of a natural binding partner for the target cell surface molecule and binds competitively to the target cell surface molecule, while in other embodiments, the small organic molecule binds non-competitively to the target cell surface molecule.

In some embodiments, the membrane penetration domain is a protein, protein fragment, polypeptide, or oligopeptide. In certain embodiments, the membrane penetration domain is a polypeptide having between about 3 to about 35 amino acids.

In an embodiment, the membrane penetration domain is the penton base protein or a fragment thereof from Adenovirus. The penton base protein normally mediates cell-binding, entry and cytosolic penetration of adenovirus (for example, adenovirus serotype 5) during the early stages of infection. The penton base may comprise an RGD motif (Arg-Gly-Asp). As used herein, "PB" refers to a penton base segment.

In some embodiments, the payload binding domain is a protein, protein fragment, polypeptide, or oligopeptide. In certain embodiments, the membrane penetration domain is a polypeptide having between about 3 to about 35 amino acids.

In one embodiment, the payload binding domain is a decalysine motif, also referred to as "K10." The decalysine motif comprises ten lysine residues.

In some embodiments, the payload that binds to the payload binding domain binds is a nucleic acid. In some embodiments, the nucleic acid is selected from the group consisting of double stranded deoxyribonucleic acid (dsDNA), single stranded deoxyribonucleic acid (ssDNA), ribonucleic acid (RNA), messenger ribonucleic acid (mRNA), transfer ribonucleic acid (tRNA), ribosomal ribonucleic acid (rRNA), small interfering ribonucleic acid (siRNA), single stranded ribonucleic acid (ssRNA), and oligonucleotides (whether single stranded or double stranded).

In certain embodiments, the binding of the payload binding domain to the payload is through a process selected from the group consisting of electrostatic interactions, electrophilic interactions, hydrophilic interactions (van der Waals forces), hydrogen binding, or covalent binding.

In various embodiments, the ligand in the drug delivery molecule targets a cell surface molecule on a cancer cell. In an embodiment, the cell surface molecule is a receptor on a cancer cell.

In an embodiment, described herein is a drug delivery molecule that includes a ligand that targets a cell surface molecule, a membrane penetration domain and a payload binding domain, wherein the ligand is Internalin B (InlB) or a fragment thereof or a variant thereof, the membrane penetration domain is the penton base protein or a fragment thereof and the payload binding domain is a decalysine motif. Internalin B targets the cell surface protein c-Met. The natural ligand of c-Met is hepatocyte growth factor (HGF). HGF forms a tetramer and requires disulfide bond formation. Internalin B, obtained from *Listeria monocytogenes* also recognizes and bind c-MET, but does not tertamerize or require disulfide bond formation. Internalin B can be expressed as a fusion protein and the fusion protein also binds to c-Met. InlB does not compete with HGF. In some embodiments, the drug delivery molecule comprising InlB, penton base protein and decalysine motif may further comprise a cytotoxic agent, such as corrole compounds. Corrole compounds are porphyrin-like molecules. These compounds can chelate a number of different metals (such as iron, gallium, manganese etc.), non-covalently bind carrier proteins, are cytotoxic and cannot penetrate cells without carrier proteins.

In other embodiments, the ligand targets the cell surface molecule CD4, or alternatively, CD19 or CD20. In further embodiments, the ligand targets one of the human epidermal growth factor receptors (HER), for example HER2 or HER3. In another embodiment, the ligand targets an integrin.

In various embodiments, the drug delivery molecule further comprises a therapeutic agent. The therapeutic agent forms a complex with the payload binding domain. In various embodiments, therapeutic agents include but are not limited to alkylating agents, antimetabolites, anti-tumor antibiotics, mitotic inhibitors, corticosteroids, cytotoxic agents or combinations thereof. The complex between the therapeutic agent and the payload binding domain may be covalent or non-covalent. In some embodiments, non-covalent complexes may be via any one or more of van der Waals forces, hydrogen bonding, electrostatic interactions, hydrophobic/hydrophilic interactions. In some embodiments, the interactions between the therapeutic agent and the payload binding domain may be mediated by a linker. In some embodiments, the therapeutic agent is doxorubicin or a corrole compound.

Also described herein are methods for treating cancer in a subject in need thereof. The methods comprise identifying a subject in need of the treatment and providing a composition that includes a drug delivery molecule and administering an effective amount of the composition to the subject so as to treat cancer. In various embodiments, the drug delivery molecule includes a ligand that targets a receptor on a cell surface, a membrane penetration domain and a payload binding domain and further comprises a therapeutic agent as described herein.

Also described herein are methods for inhibiting the progression of cancer in a subject in need thereof. The methods comprise identifying a subject in need of the treatment and providing a composition that includes a drug delivery molecule and administering an effective amount of the composition to the subject so as to inhibit the progression of cancer. In various embodiments, the drug delivery molecule includes a ligand that targets a receptor on a cell surface, a membrane penetration domain and a payload binding domain and further comprises a therapeutic agent as described herein.

Also described herein are methods for preventing cancer metastasis in a subject in need thereof. The methods comprise identifying a subject in need of the prevention and providing a composition that includes a drug delivery molecule and administering an effective amount of the composition to the subject so as to prevent cancer metastasis. In various embodiments, the drug delivery molecule includes a ligand that targets a receptor on a cell surface, a membrane penetration domain and a payload binding domain and further comprises a therapeutic agent as described herein.

Also provided herein are methods for treating, inhibiting or preventing metastasis of drug resistant cancers (for example, cancer resistant to EGFR tyrosine kinase inhibitor). The methods comprise identifying a subject in need of the treatment and providing a composition that includes a drug delivery molecule and administering an effective amount of the composition to the subject so as to treat, inhibit or prevent metastasis of drug resistant cancers. In various embodiments, the drug delivery molecule includes a ligand that targets a receptor on a cell surface, a membrane penetration domain and a payload binding domain and further comprises a therapeutic agent as described herein. In an embodiment, the drug resistant cancers over-express a receptor selected from the group consisting of c-Met, HER2, CD4, and CD20.

Also provided herein are methods of delivering a therapeutic compound to the brain. The methods comprise identifying a subject in need of such delivery and providing a composition that includes a drug delivery molecule and administering an effective amount of the composition to the subject. In various embodiments, the drug delivery molecule includes a ligand that targets a receptor on a cell surface, a membrane penetration domain and a payload binding domain and further comprises a therapeutic agent as described herein. The compositions described herein surprisingly cross the blood-brain barrier and deliver the payload to the cells in the brain. Thus, these compositions are uniquely suited for the treatment of cancers, for example metastatic cancers, in the brain.

In various aspects of the therapeutic methods described herein, the drug delivery molecule in the composition includes a ligand that targets a receptor on a cell surface, a membrane penetration domain and a payload binding domain, wherein the ligand is Internalin B (InlB) or a fragment thereof or a variant thereof, the membrane penetration domain is the penton base protein or a fragment thereof and the payload binding domain is a decalysine motif. The drug delivery molecule further comprises a therapeutic agent such as doxorubicin or corrole compounds.

Therapies

Another aspect of the invention relates to treating cancer (for example, leukemia, myeloma, B-cell lymphomas (Hodgkin's lymphomas and/or non-Hodgkins lymphomas), brain cancer, breast cancer, colorectal cancer, lung cancer, hepatocellular cancer, kidney cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, prostate cancer, androgen-dependent prostate cancer, and androgen-independent prostate cancer) by administering an effective amount of a composition that includes the drug delivery molecules complexed with therapeutic agents as described herein. In some embodiments, the therapeutic agent can be any chemotherapeutic drug that is applicable to treating the particular type of cancers. The therapeutic agent can be an organic molecule, a biological molecule (e.g., a peptide or a nucleic acid), or a combination thereof. In various embodiments, therapeutic agents include but are not limited to alkylating agents, antimetabolites, anti-tumor antibiotics, mitotic inhibitors, corticosteroids, cytotoxic agents or combinations thereof. In an embodiment, the therapeutic agent is a corrole compound. In an embodiment, the therapeutic agent is an siRNA molecule.

In some embodiments, the composition comprising an effective amount of the drug delivery molecule complexed with a therapeutic agent is administered with one or more chemotherapeutic agents, such as those set forth herein. Effective amounts of the composition and the chemotherapeutic agent may be administered sequentially or concurrently.

In some embodiments, the administering is systemic. In some embodiments, the administering is local. A variety of means for administering the composition to subjects are known to those of skill in the art. In some aspects of all the embodiments of the invention, the compositions are administered through routes, including ocular, oral, parenteral, intravenous, intramuscular, subcutaneous, transdermal, airway (aerosol), pulmonary, cutaneous, topical, or injection administration.

Additional therapies that may be used with the compositions comprising an effective amount of the drug delivery molecule complexed with a therapeutic agent to treat cancer include but are not limited to surgery, radiation, immunotherapy, vaccine or combinations thereof. The additional therapies may be administered sequentially or simultaneously with therapies comprising administering an effective amounts of a compositions comprising an effective amount of the drug delivery molecule complexed with a therapeutic agent to treat cancer (for example, melanoma or ovarian carcinoma).

In some embodiments, chemotherapeutic agents may be selected from any one or more of cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: treosulfan, and trofosfamide; plant alkaloids: vinblastine, paclitaxel, docetaxol; DNA topoisomerase inhibitors: doxorubicin, epirubicin, etoposide, camptothecin, topotecan, irinotecan, teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.).

As described herein, in various embodiments, therapies include, for example, radiation therapy. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (1-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

As described herein, in various embodiments, therapies include, for example, immunotherapy. Immunotherapy may comprise, for example, use of cancer vaccines and/or sensitized antigen presenting cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

As described herein, in various embodiments, therapies include, for example, hormonal therapy, Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

The duration and/or dose of treatment with anti-cancer therapies may vary according to the particular anti-cancer agent or combination thereof. An appropriate treatment time for a particular cancer therapeutic agent will be appreciated by the skilled artisan. The invention contemplates the continued assessment of optimal treatment schedules for each cancer therapeutic agent, where the genetic signature of the cancer of the subject as determined by the methods of the invention is a factor in determining optimal treatment doses and schedules.

In various embodiments, the subject for whom predicted efficacy of an anti-cancer therapy is determined, is a mammal (e.g., mouse, rat, primate, non-human mammal, domestic animal such as dog, cat, cow, horse), and is preferably a human. In another embodiment of the methods of the invention, the subject has not undergone chemotherapy or radiation therapy. In alternative embodiments, the subject has undergone chemotherapy or radiation therapy (e.g., such as with cisplatin, carboplatin, and/or taxane). In related embodiments, the subject has not been exposed to levels of radiation or chemotoxic agents above those encountered generally or on average by the subjects of a species. In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient, or e.g., the subject is given the anti-cancer therapy prior to removal of the cancerous tissue.

Pharmaceutical Compositions

In various embodiments, the present invention provides pharmaceutical compositions including a pharmaceutically acceptable excipient along with a therapeutically effective amount of the drug delivery molecule described herein so as to treat cancer (for example, leukemia, myeloma, B-cell lymphomas (Hodgkin's lymphomas and/or non-Hodgkins lymphomas), brain cancer, breast cancer, colorectal cancer, lung cancer, hepatocellular cancer, kidney cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, prostate cancer, androgen-dependent prostate cancer, and androgen-independent prostate cancer). In various embodiments, the drug delivery molecule includes a ligand that targets a receptor on a cell surface, a membrane penetration domain and a payload binding domain. The drug delivery molecule further comprises a therapeutic agent that complexes with the drug delivery molecule as described herein. In various embodiments, the drug delivery molecule delivers the therapeutic agent to the target cancer cell.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, intraocular, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection, either intravenously or intraperitoneally. Methods for these administrations are known to one skilled in the art.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Before administration to patients, formulants may be added to the agents. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

In some embodiments, polymers as formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Additionally, the compositions can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546 which are all hereby incorporated by reference in their entireties. Preferred polymers are polyoxyethylated polyols and polyethylene glycol (PEG). PEG is soluble in water at room temperature and in some embodiments, has an average molecular weight between 1000 and 40,000, between 2000 and 20,000, or between 3,000 and 12,000. In some embodiments, PEG has at least one hydroxy group, such as a terminal hydroxy group. The hydroxy group may be activated to react with a free amino group on the inhibitor. However, it will be understood that the type and amount of the reactive groups may be varied to achieve a covalently conjugated PEG/antibody of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a molecular weight in the same range as PEG. The structure for POG is shown in Knauf et al., 1988, J. Bio. Chem. 263:15064-15070 and a discussion of POG/IL C 2 conjugates is found in U.S. Pat. No. 4,766,106, both of which are hereby incorporated by reference in their entireties.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The dosage and mode of administration will depend on the individual. Generally, the compositions are administered so that antibodies are given at a dose between 1 µg/kg and 20 mg/kg, between 20 µg/kg and 10 mg/kg, between 1 mg/kg and 7 mg/kg. In some embodiments, it is given as a bolus dose, to increase circulating levels by 10-20 fold and for 4-6 hours after the bolus dose. Continuous infusion may also be used after the bolus dose. If so, the antibodies may be infused at a dose between 5 µg/kg/minute and 20 µg/kg/minute, or between 7 µg/kg/minute and 15 µg/kg/minute.

Kits

The invention also provides a kit to treat, inhibit and/or prevent metastasis of cancer in a subject in need thereof. The kit comprises a composition comprising a drug delivery molecule complexed with a therapeutic agent, as described herein and instructions for use of the composition for treating, inhibiting and/or preventing metastasis of cancer in subjects in need thereof.

The kit is an assemblage of materials or components, including at least one of the inventive compositions. Thus, in some embodiments the kit contains a composition including a drug delivery molecule complexed with a therapeutic agent, as described above.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat, reduce the severity of, inhibit or prevent neutropenia in a subject. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a bottle used to contain suitable quantities of an inventive composition containing the catalytically active antibody having sialidase activity produced by the methods described herein. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1: Delivery of Single-Stranded Oligonucleotide and Synthetic mRNA

The delivery of synthetic mRNA is an improved alternative to gene delivery. Gene delivery vectors must breach the nucleus to enable gene expression, whereas mRNA only requires delivery into the cytoplasm for translation of protein products. Such as approach is used to express, for example, the so-called Yamanaka factors for inducing pluripotency in somatic cells. While traditional "lipofection" may be useful for delivery of mRNA in vitro, this and similar systems are not effective in vivo.

The disclosed targeted cell penetration protein, HerPBK10, has proven efficacy for nucleic acid and drug delivery in vivo. The related protein, PBK10, has also been developed for gene and drug delivery. HerPBK10 facilitates targeted binding and penetration of cells via interaction with the human epidermal growth factor receptor (HER3), and PBK10 does so via integrin interaction.

Below, the utility of HerPBK10 and PBK10 for the delivery of single-stranded oligonucleotide and synthetic mRNA is demonstrated.

HerPBK10 transports a labeled oligonucleotide in MDA-MB-435 cells. To determine whether HerPBK10 can mediate single-stranded oligonucleotide delivery, a Cy3-labeled oligonucleotide (50 pmol) was incubated with HerPBK10 (5 µg) or Lipofectamine 2000 (Invitrogen, Carlsbad, Calif., USA), a commercial transfection reagent as a comparative control, in 0.1 M HEPES/Optimem I (Invitrogen; Carlsbad, Calif., USA) for 20 minutes at RT. The resulting mixture was added to MDA-MB-435 cells, which express HER, and incubated for 1 h at 37° C. Cells were fixed in 4% PFA for 15' at RT and processed for immunofluorescence against HerPBK10. Cells were counterstained with DAPI to identify nuclei. Images were acquired using a Leica SP2 laser scanning confocal microscope. Lipofectamine-mediated uptake resulted in oligonucleotide localization inside the cells, as expected (FIG. 1A). Importantly, HerPBK10 colocalized with the oligonucleotide during binding and uptake of HerPBK10-oligo complexes (FIG. 1B), suggesting that HerPBK10 mediates transport of the oligonucleotide into cells.

PBK10 Mediates mRNA Delivery.

Figure 2A:
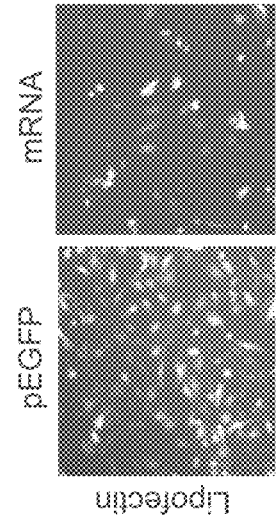
Figure 2B:
Figure 2C:
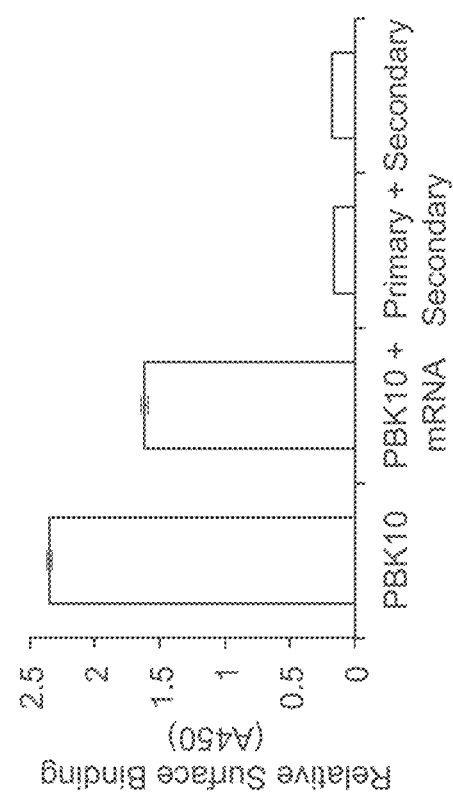

A 1 kb synthetic mRNA encoding GFP (FIG. 2A) was used to test the ability of PBK10 to mediate delivery into cells for protein expression. GFP expression from mRNA delivered by Lipofectin was compared to a GFP-expressing plasmid delivered by Lipofectin. When delivered by Lipofectin, the mRNA expressed GFP at levels in HeLa cells that were detectable by fluorescence microscopy (FIG. 2B). PBK10 and synthetic mRNA encoding GFP were mixed at a 20:1 weight ratio of PBK10:mRNA for ~20 min at RT in HEPES-buffered saline (HBS) and then added to adherent HeLa cells at ~50-70% confluency. Thus, PBK10 formed complexes with mRNA similar to the gene delivery complexes that PBK10 had previously been developed to deliver (FIG. 2C).

Figure 2D:
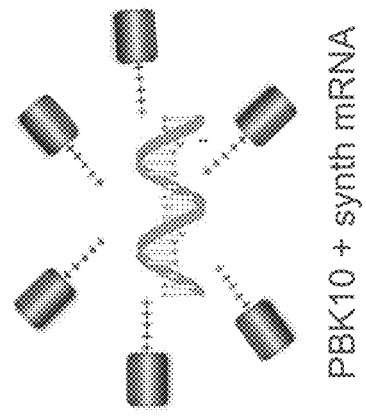

The ability of PBK10 to mediate delivery was examined by first assessing the cell binding of complexes made between PBK10 and the mRNA. PBK10-mRNA complexes were incubated on the HeLa cells on ice to promote receptor binding but not internalization, then the cells were washed to remove free (unbound) complexes and processed by ELISA to identify cell surface-bound complexes using a primary antibody against PBK10. An ELISA-based detection of cell surface binding showed that the complexes bind (PBK10+mRNA) to the cells (FIG. 2D). Cells were also processed for immunofluorescence against PBK10 alone after incubation of PBK10 (without mRNA) on cells. To verify uptake of cell-bound complexes (E), cells were incubated with complexes on ice as described earlier, washed, then warmed at 37° C. to promote internalization. Cells were fixed at the indicated time points after warming and processed for immunofluorescence against PBK10 (green). Cells were counterstained with rhodamine phalloidin and DAPI to identify actin (red) and nuclei (blue), respectively. Images were acquired using a Leica SPE laser scanning confocal microscope. The findings show that the complexes underwent time-dependent internalization into HeLa cells (FIG. 2E). A separate set of HeLa cells were fixed and processed for immunofluorescence against GFP at ~24 h after the cells were incubated with PBK10-mRNA complexes. The findings show that GFP expression was detectable after PBK10-mediated delivery of mRNA, albeit at low frequency (few cells) (FIG. 2D). The optimal weight ratio of PBK10:mRNA to enable sufficient GFP expression (detectable by immunofluorescence) was 20 (FIG. 2E). These findings altogether show that it was possible to deliver a mRNA by PBK10 or HerPBK10, since both proteins interact with nucleic acids in similar fashion.

Example 2: A Protein Nano-Construct Targeted to c-Met

The receptor tyrosine kinase (RTK), c-MET, and its endogenous ligand, hepatocyte growth factor (HGF), contribute to cell migration, morphogenic differentiation, and organization of three-dimensional tubular structures as well as cell growth and angiogenesis during normal tissue development. However, dysregulation of c-MET and HGF can contribute to tumor progression, and in such circumstances, correlates with poor prognosis in a broad range of human cancers.

Cell surface elevation of c-MET has been associated with drug-resistance, including acquired resistance to current signal-blocking therapies, and thus has become an important biomarker for RTK-targeted therapy. Whereas the majority of therapies targeting RTKs are designed to inhibit downstream signaling pathways that support tumor survival, tumors that initially respond to such treatment almost universally acquire resistance to signal inhibition while a significant population are already inherently resistant to such signal-blocking therapies.

Tumor-targeting strategies that do not require signal inhibition may prove more effective on c-MET positive cancer cells. This may be addressed by ligands that recognize c-MET to trigger cell uptake of attached therapeutics, thus bypassing the need to block signaling. While HGF has the potential to accomplish this, its requirement for tetramerization and disulfide bonding presents technical complications for therapeutics development. An alternative, and potentially superior ligand for c-MET targeting may possibly be derived from a bacterium that causes food-poisoning.

The human pathogen, *Listeria monocytogenes*, binds c-MET to invade host cells through its surface proteins called Internalins. Specifically, Internalin B (InlB) triggers receptor-mediated endocytosis after c-Met binding. InlB and HGF recognize different regions of c-Met, and InlB does not require tetramerization or disulfide bonds for binding. Consequently, InlB may lend itself to the nanobiologic strategy for tumor-targeting that we have previously established for targeting other receptors such as the human epidermal growth factor receptor (HER).

PBK10 is a recombinant protein derived from the adenovirus capsid penton base that can mediate gene and drug delivery into cells through the membrane penetrating activity of the penton base. It has been shown that PBK10 can be targeted to tumor cells when fused to tumor-specific ligands. In this study, the receptor-binding site of InlB is produced as a recombinant fusion to PBK10 to produce the new protein, InlB-PBK10, which mediates the targeted-delivery of cytotoxic agents to c-MET positive cancer cells.

The findings show that InlB-PBK10 can be produced as a soluble fusion protein that recognizes c-MET on a variety of tumor cell lines, and undergoes rapid internalization after cell binding. InlB-PBK10 forms ~10-20 nm diameter nanoclusters with toxic compounds such as corroles, and mediates corrole penetration into the cytoplasm after cell entry, causing tumor cell death. Thus, Inl-PBK10 is a novel construct for mediating the targeted delivery of toxic molecules to MET-expressing tumors.

BACKGROUND

C-MET as a Tumor Biomarker.

Mesenchymal Epithelial Transition factor or MET is a receptor tyrosine kinase (RTK) that was first discovered as an activated oncogene. The endogenous ligand for MET, Hepatocyte Growth Factor (HGF), also known as fibroblast-derived cell motility factor or Scatter Factor (SF), normally activates MET to induce cell proliferation, motility, survival and differentiation pathways. MET and HGF are mainly expressed in cells of epithelial and mesenchymal origin, respectively. The paracrine signaling between HGF and MET mediates epithelial-mesenchymal interactions that regulate tissue growth and morphogenic differentiation. HGF-MET signaling in normal tissue contributes to embryogenesis, organogenesis, angiogenesis, wound healing and tissue regeneration, whereas aberrant signaling of this pathway is associated with tumor development and progression, tumor cell invasion and metastasis.

C-MET consists of an amino (N)-terminal extracellular domain, a membrane spanning segment and a carboxy (C)-terminal intracellular kinase domain. The extracellular region consists of an amino (N)-terminal Semaphorin (Sema) domain adjacent to a PSI domain (present in plexins, semaphorins, and integrins) followed by four immunoglobulin (Ig)-like domains, which together comprise the binding site for HGF. Receptor binding by HGF leads to dimerization of MET, activating signaling through ERK1/2, AKT and STAT3, phosphoinositide 3-kinase (PI-3K), Ras-Raf-MAPK, and phospholipase C. Ligand-triggered endocytosis of MET occurs through dynamin and clathrin-dependent pathways that mediate trafficking through both degradative and recycling endocytotic routes.

Dysregulation of c-MET signaling occurs through several mechanisms, including overexpression and constitutive kinase activation with or without gene amplification, kinase-domain mutation, and paracrine/autocrine activation of c-MET by overexpression of HGF. Ligand-independent activation of c-MET also disrupts normal HGF-MET signaling and can result from mutations causing constitutive dimerization, as well as hypoxic conditions. The latter can activate HIF-1α-induced transcription of MET causing elevated protein levels amplifying HGF signaling and promoting invasion.

It has been generally accepted that the heterogeneous expression of various RTKs across the tumor is a major mechanism of resistance in many types of cancer. Therapies aimed at inhibiting one specific RTK are often not successful due to upregulation or ligand stimulation of other RTKs that, in turn, sustain signaling of factors critical for cell-survival, including PI3K and mitogen-activated protein kinase (MAPK). This mechanism of resistance was identified in studies showing that resistance to EGFR inhibitors is associated with compensatory upregulation of MET signaling in non-small cell lung cancer as well as other tumors, including breast cancer. Taken altogether, c-MET is a valid candidate for therapeutic intervention since it is associated with various types of cancer, poor prognosis and metastasis, and could be a useful biomarker for identifying and targeting resistant tumors.

The therapies currently targeted at the HGF/MET pathway in the clinic consist of either antibodies directed against HGF (Ficlatuzumab) or MET (Onartuzumab), or small molecule inhibitors (Tivantinib or ARQ197) directed at the MET kinase domain. A problem with all of these approaches is their reliance on signal inhibition for therapeutic efficacy, which is prone to the compensatory RTK cross-talk mentioned earlier, facilitating the development of resistance. There is an increasing interest in using combination therapies to block or disrupt the function of multiple RTKs, particularly EGF-R and MET given the significant cross-talk between these two receptors. While in vitro studies testing this approach have shown promise on tumor cell lines such as lung, breast, gastric and colorectal cancer, clinical trials testing this approach are still underway and remain inconclusive.

A Bacterial Pathogen Protein as a Potential c-MET Targeting Agent. Internalin B (InlB) is a protein displayed on the surface of the human bacterial pathogen, *L. monocytogenes* (Lm), and facilitates the entry of Lm into non-phagocytic cells through binding to c-MET. InlB is a member of the larger family of Lm internalin proteins which are comprised of an N-terminal helical cap domain followed by differing numbers of leucine-rich repeats (LRRs) adjacent to an immunoglobulin-like inter-repeat (IR) region. Unlike other internalins, InlB structure also contains a B-repeat and three GW modules at the C-terminal end. InlB321, a fragment of InlB capable of binding to c-MET with high affinity, consists of protein domains known as the Cap, LRR (protein-protein interaction domain), and IR regions. The binding of InlB321 to MET occurs through its two domains: LRR and IR, which bind to the Ig1 and Sema domain of MET respectively.

InlB has several advantages over HGF as a potential tumor-targeting ligand. HGF is a heterodimeric protein containing 20 sulfide bonds and requires cleavage of a pro-protein into assembled subunits, which may pose complications for recombinant production, especially as a fusion to exogenous protein domains. In contrast, InlB321 has already been produced as a recombinant soluble ligand in *Escherichia coli* and can tolerate fusion to other proteins (FIG. 3A). In vitro studies have demonstrated that the InlB321 peptide can trigger receptor-mediated internalization after MET binding, which is conducive to its use as a nano-delivery agent. It is also important to note that there is no overlap between the HGF binding site of MET with that of InlB321 (FIG. 3B); therefore, there is no competition between these two ligands for binding to MET.

In the present study this peptide is re-engineered by producing it as a recombinant fusion to the Ad5 penton base (PB) that is modified by a decalysine sequence (K10) at the carboxyl (C)-terminus end. The resulting multi-domain protein, InlB-PBK10, contains functions for transport of anionic cargoes such nucleic acids or corroles (mediated by the K10 domain), targeted binding and internalization (mediated by the InlB321 domain), and membrane penetration and intracellular trafficking (mediated by the PB domain). Results are presented for the construction of the InB-PBK10 fusion gene, the production of the fusion protein encoded by this recombinant gene, the characterization of the protein with respect to its ability to bind to MET and enter cells, and the evaluation of its ability to deliver cytotoxic payloads in vitro.

Results

A Recombinant Gene can be Constructed to Encode InlB-PBK10.

The strategy for producing the InlB-PBK10 gene construct involved a two-step cloning method entailing polymerase chain reaction (PCR) amplification of InlB321 for cloning into the pRSET-A bacterial expression plasmid, followed by insertion of PBK10 at the 3' end of the InlB321 sequence. To accomplish this, oligonucleotide primers were designed to introduce restriction sites by PCR into InlB321 to join this sequence with PBK10 for "in-frame" insertion into the expression plasmid, pRSET-A.

Our forward and reverse oligonucleotide primers contained the following sequences respectively:

(SEQ ID NO: 1)
5'-AGTGAGCTCGAGACTATCACTGTG-3'
and (SEQ ID NO: 2)
5'-GTTGGTGACTTTCTCCCACCTTCACCACCTTCATCTAGATATCCATGGTAT-3'.

The restriction site, SacI, was introduced in the forward primer to place the InlB321 reading frame contiguous with the N-terminal poly-histidine sequence encoded by pRSET-A. BglII and KpnI restriction sites were introduced into the reverse primer. SacI and KpnI were used to insert InlB321 into pRSETA, and BglII was used for subsequent insertion of PBK10 just 3' to the InlB321 coding sequence. A sequence encoding a Gly-Gly-Ser-Gly-Gly-Ser (SEQ ID NO:3) amino acid motif was included in the reverse primer to incorporate a short flexible linker between InlB321 and PBK10. A high-fidelity polymerase was used to ensure that mutations were not introduced into the InlB321 PCR product.

The 800 bp InlB321 PCR product was ligated into pRSETA at the SacI and KpnI restriction sites, producing the plasmid construct, pRSETA-InlB. PBK10 was then inserted into pRSETA-InlB at restriction sites BglII and HindIII. To do so, PBK10 was excised from the plasmid construct, pRSETA-PBK10 at restriction sites BamHI and HindIII and ligated into double digested pRSETA-InlB, resulting in the pRSETA-InlB-PBK10 construct (FIG. 4A). We also produced the construct, pRSETA-GFP-InlB, that encodes InlB321 as a carboxy [C]-terminal fusion to green fluorescent protein (GFP) for possible future in vitro and in vivo imaging experiments. This construct was made by digesting the 800 bp InlB PCR product described earlier with SacI and BglII, and ligating this into the pRSETA-GFP plasmid, which places the InlB insert in-frame with the coding sequence of GFP (FIG. 4B). All constructs were double digested and evaluated by electrophoresis using a 1% agarose gel to confirm the presence of the expected bands (FIG. 4C). Additionally, all three constructs were sequenced to confirm their identity as well as verify that mutations were not introduced into the reading frames.

Recombinant Proteins InlB, InlB-PBK10 and GFP-InlB can be Produced in Bacteria.

All three plasmid constructs described earlier (pRSET-InlB, pRSET-InlB-PBK10, and pRSET-GFP-InlB) were transformed into the E. coli strain, BLR (DE3) pLysS, for subsequent protein expression and purification, as described in the Methods. This strain is more tolerant of repeat sequences in contrast to more traditional (i.e. BL21) expression strains, thus enabling the ability to obtain full-length proteins containing C-terminal polylysines. Meanwhile, the pRSET-A plasmid encodes proteins as N-terminal fusions to a polyhistidine sequence. This histidine (His)-tag enables affinity purification using nickel-chelating resin and provides an epitope for recognition by anti His-tag antibodies.

Figure 5:
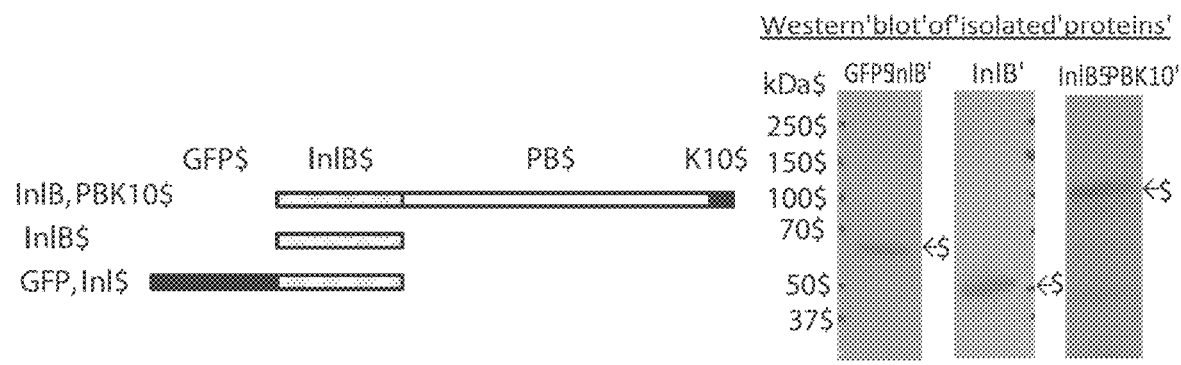
FIG. 5 is the results of a Western blot showing the recombinant proteins InlB, InlB-PBK10 and GFP-InlB are produced in bacteria.

All three constructs produced soluble proteins (InlB, InlB-PBK10, and GFP-InlB) in bacteria, which could be isolated by metal chelate affinity chromatography using nickel-conjugated resin, as described in the Methods. Anti-His tag antibodies recognized all three proteins, which migrated by denaturing gel electrophoresis at the predicted molecular weights of ~37 kDa (InlB), ~100 kDa (InlB-PBK10) and ~63 kDa (GFP-InlB) (FIG. 5).

The Surface Level of c-MET Varies Among Different Tumor Cell Lines.

Figure 6:
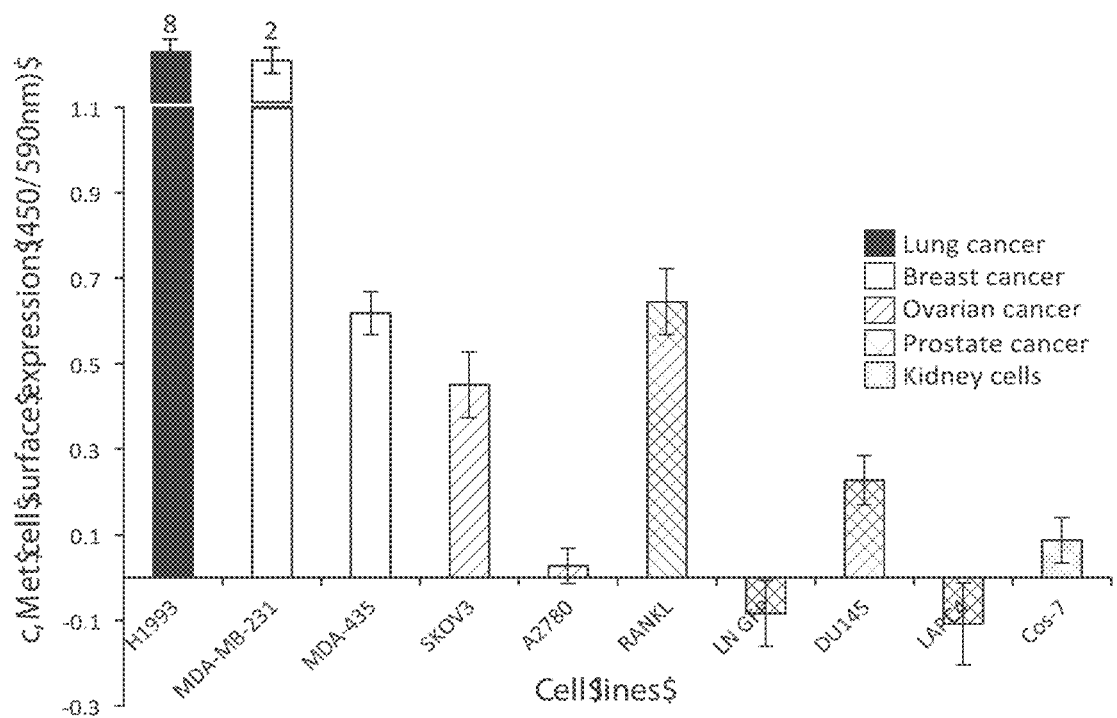
FIG. 6 is a graph showing the surface level of c-MET varies among different tumor and non-tumor cell lines. Relative receptor levels on the surface of non-permeabilized cells as measured by a cell surface ELISA performed in a 96-well format are shown. ELISA results show that the H1993 (lung cancer cell line) and MDA-MB-231 (breast cancer cell line) are among the cells with the highest cell surface levels of c-MET. RANKL (prostate cancer cell line) and MDA-MB-435 (breast cancer cell line) display moderate levels while LN-GFP (prostate cancer cell line) and Cos-7 (African green monkey kidney fibroblast) display low levels of cell surface c-MET.

The first objective in characterizing InlB-PBK10 was to determine whether this protein recognizes c-MET on tumor cells. Most of the literature regarding c-MET levels associated with different tumor cell lines is based either on total c-MET protein expression or RNA expression, and thus is not informative with regard to the level of c-MET displayed on the cell surface. Therefore, it was important to first determine the relative cell surface levels of c-MET on the panel of cell lines available for our use. This proved to be an initial challenge because the majority of antibodies available for such assessments have been generated against cytosolic domains of c-MET, and used to evaluate mechanisms of c-MET expression and activation. For this study, the MET3 antibody, developed specifically against cell surface c-MET, was used. We used a cell-surface ELISA to measure relative cell-surface levels of c-MET on a variety of cell lines. Briefly, this approach enables us to measure relative receptor levels on the surface on non-permeabilized cells and can be performed in a 96-well format, allowing both multiple replicates as well as the conservation of precious reagents. Our ELISA results show that the H1993 (lung cancer cell line) and MDA-MB-231 (breast cancer cell line) are among the cell lines with the highest surface levels of c-MET. RANKL (prostate cancer cell line) and MDA-MB-435 (breast cancer cell line) display moderate levels while LN-GFP (prostate cancer cell line) and Cos-7 (African green monkey kidney fibroblast) display low levels of cell surface c-MET (FIG. 6).

The InlB-Derived Peptide Recognizes c-MET.

Figures 7A, 7B:
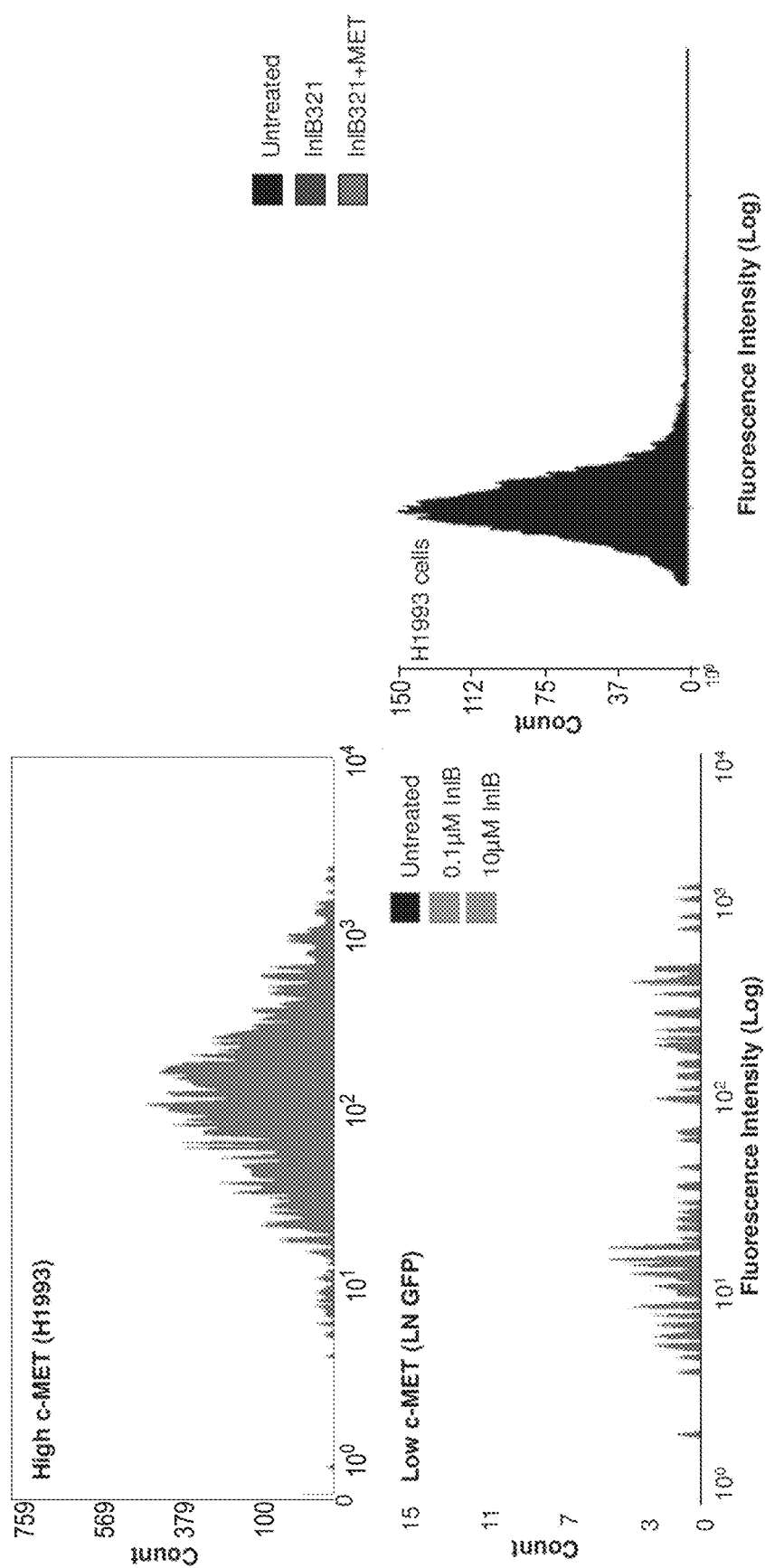
FIGS. 7A-E show the results of the experiments showing the InlB-derived peptide recognizes c-MET.

In order to assess the receptor-specificity of the targeting ligand, we used fluorescence activated cell sorting (FACS) to measure the relative level of InlB bound to c-MET positive cells. Two tumor cell lines were tested for the binding of InlB: one tumor cell line with high expression of c-MET (H1993) and another tumor cell line with low expression of c-MET (LN GFP). InlB exhibited a proportionately higher level of binding to H1993 cells in comparison to LN GFP (FIG. 7A). To verify whether InlB is specifically bound to c-MET, we used a soluble peptide derived from the extracellular, ligand-binding domain of MET (MET peptide) as a competitive inhibitor for InlB binding. An equimolar ratio of inhibitor to ligand predicts 50% reduction in receptor binding. In agreement, equimolar (1:1) concentrations of MET:InlB reduced InlB binding to H1993 cells by 50%, indicative c-MET-selective binding. (FIG. 7B).

Cell-Binding by InlB-PBK10 Associates with c-MET Level and is Competitively Inhibited by Free Ligand.

Figures 7C, 7D:
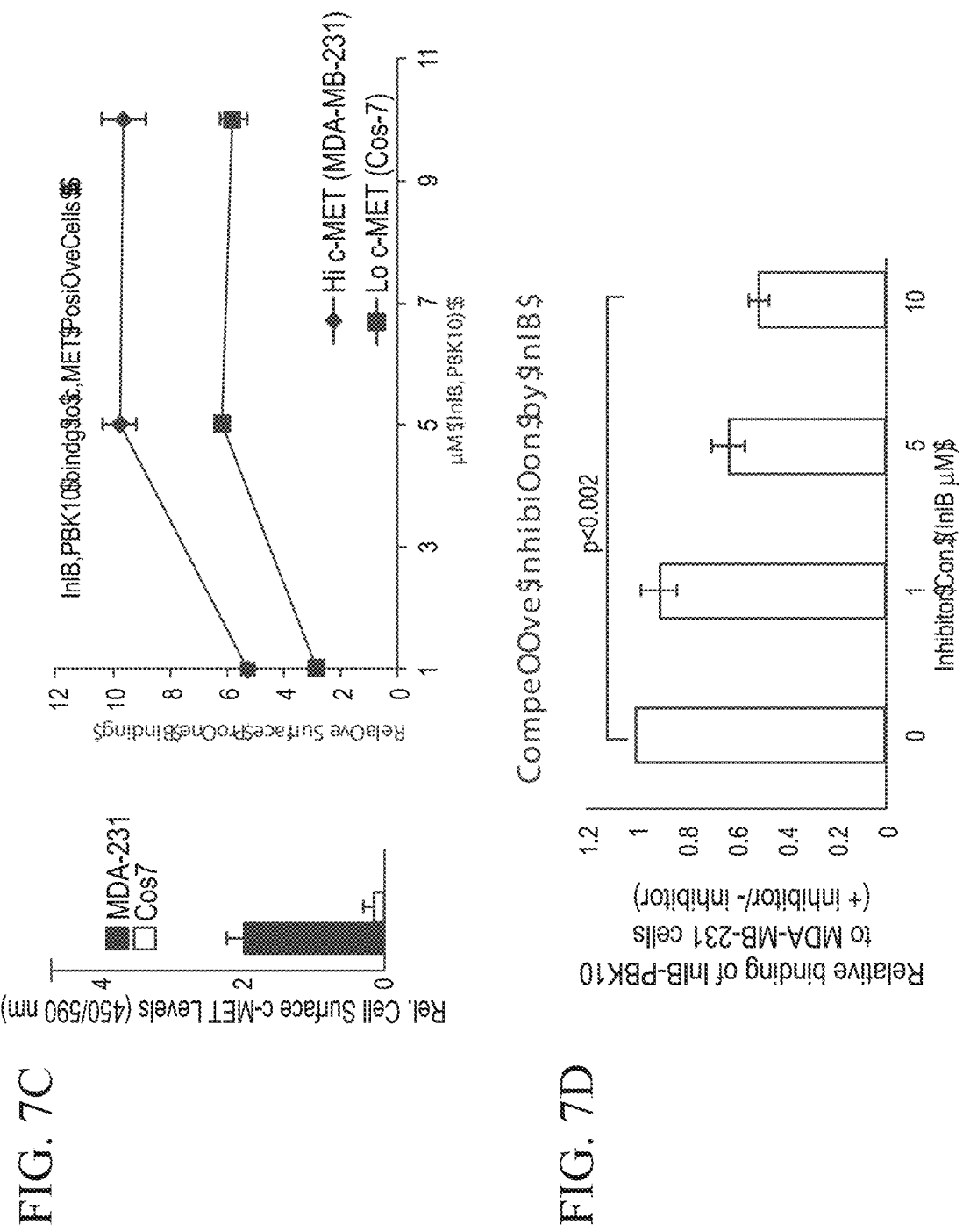

In the previous section, we showed that InlB has the capacity to bind to c-MET positive tumor cell lines through c-MET. The next goal was to test whether receptor binding by InlB would be affected when embodied as part of a fusion protein. To evaluate this, we assessed the binding of InlB-PBK10 to cell lines expressing high c-MET (MDA-MB-231) and low c-MET (Cos-7) using cell surface ELISA. InlB-PBK10 showed a higher level of binding to the cells with higher c-MET cell surface expression (MDA-MB-231) in comparison to cells expressing relatively low c-MET levels (Cos-7) (FIG. 7C). To further confirm that InlB-PBK10 recognizes c-MET, free InlB ligand was used as a competitive inhibitor. InlB-PBK10 showed decreased binding to MDA-MB-231 cells in the presence of increasing concentrations of InlB, suggesting that InlB-PBK10 binds these cells through c-MET (FIG. 7D).

InlB-PBK10 Exhibits Binding to c-MET on Cells in Suspension.

Figure 7E:
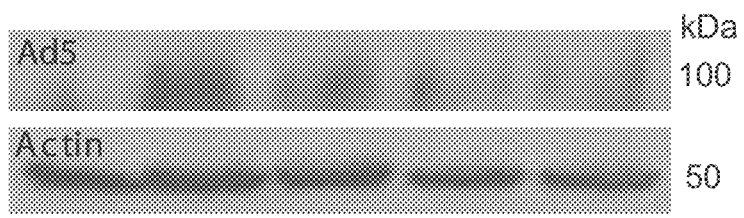
Figure 7E:
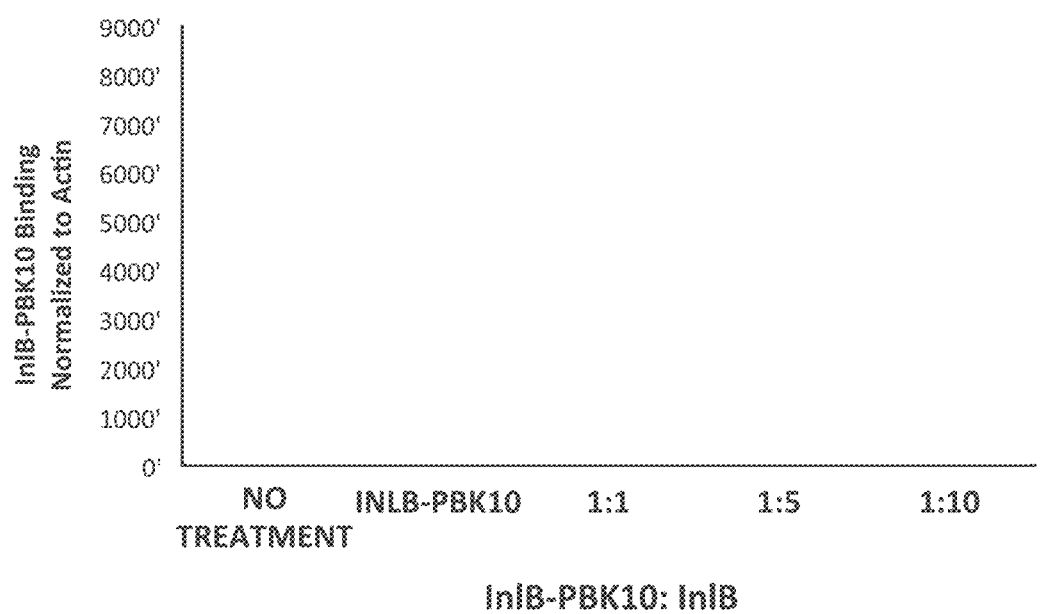

As a further confirmation of c-MET recognition, we tested whether InlB-PBK10 could bind to cells in suspension (in contrast to the previous assay which assessed binding to adherent cells). We performed a pull down assay in which we incubated the c-MET positive cell line, MDA-MB-435, in suspension with InlB-PBK10 in the presence of increasing concentrations of free InlB ligand as a competitive inhibitor. The concentrations of free InlB ligand were chosen so that the molar ratios of InlB-PBK10:InlB were 1:1, 1:5, and 1:10. InlB-PBK10 levels co-precipitating with cell pellets were then assessed by Western blotting using an antibody specific for InlB-PBK10 (Ad5 antibody, which recognizes the penton base). The levels of Inl-PBK10 binding decreased as the concentration of InlB increased, with binding nearly completely inhibited, thus verifying that InlB-PBK10 can recognize and bind c-MET on cells in suspension (FIG. 7E).

Figure 8:
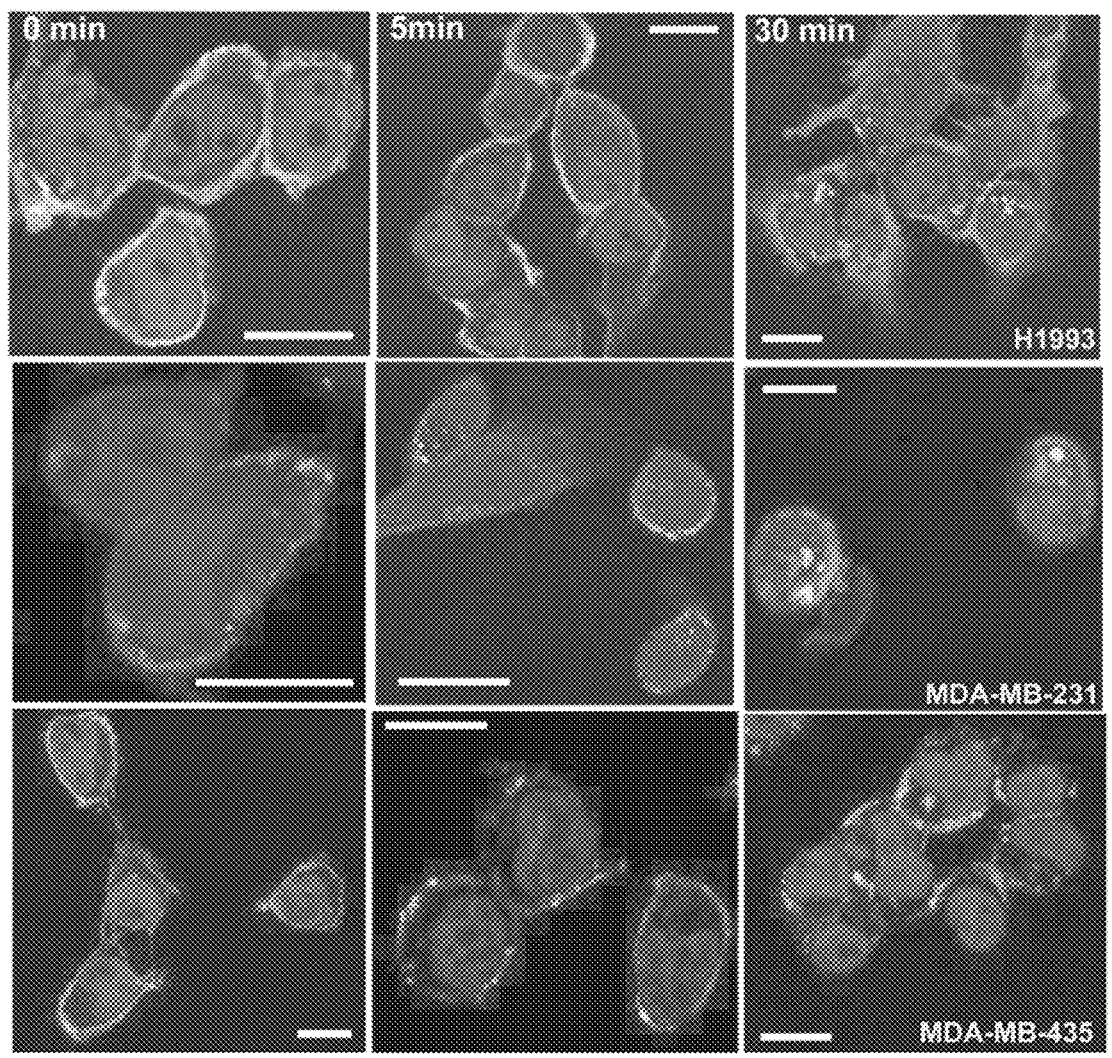
FIG. 8 shows that InlB-PBK10 internalizes into c-MET+ cells.

InlB-PBK10 internalizes into c-MET+ cells. To examine the survival and detection of InlB-PBK10 after cell uptake, we first incubated InlB-PBK10 with three different cell types, MDA-MB-231, MDA-MB-435 and H1993, at 4° C. to promote receptor binding but not internalization. To induce endocytosis, we then incubated the cells at 37° C. for the indicated times and fixed the cells at the specific time points up to 30 minutes. Immunofluorescent staining and confocal microscopy show that in all the three cell lines InlB-PBK10 (shown in green) congregated on the cell membrane and gathered into foci at the cell membrane within the first 5 minutes of binding. InlB-PBK10 then accumulated in the perinuclear region by 30 minutes. These data show that InlB-PBK10 can internalize and accumulate inside the cells within 30 minutes after cell binding (FIG. 8). Cells were fixed at the specific time points up to 30 minutes and imaged by laser scanning confocal microscopy. Red, actin; Blue, nucleus. Bar, ~10 microns.

InlB-PBK10 Delivers Toxic Molecules to c-MET+ Cells.

To evaluate the endosomolytic capacity of InlB-PBK10, we assessed whether it could mediate the cytoplasmic entry of cytotoxic agents that are inherently incapable of penetrating the cell membrane on their own. Sulfonated corroles containing gallium (III) (S2Ga or Ga-corrole) are intensely fluorescent compounds that can spontaneously assemble with proteins. These compounds cannot cross the cell membrane without a membrane-penetrating carrier to deliver them into cells to access cytoplasmic targets of toxicity. 20-22 The Medina-Kauwe lab has previously shown that Ga-corroles alone are non-toxic but can promote cell death when delivered into HER2+ tumor cells by HerPBK10.

Figure 9A:
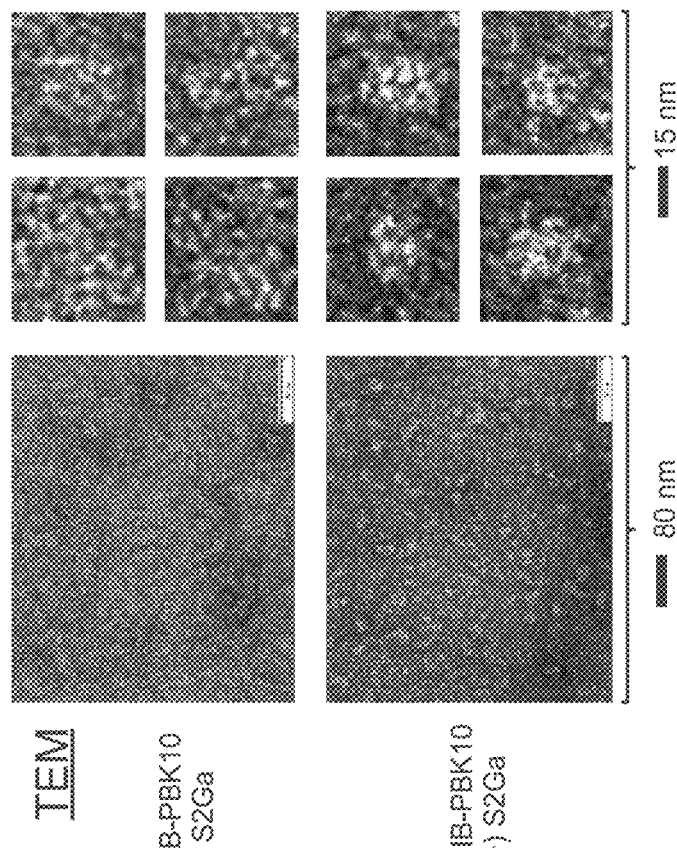
FIGS. 9A-9E show InlB-PBK10 can deliver toxic molecules to c-MET+ cells.
Figure 9A:
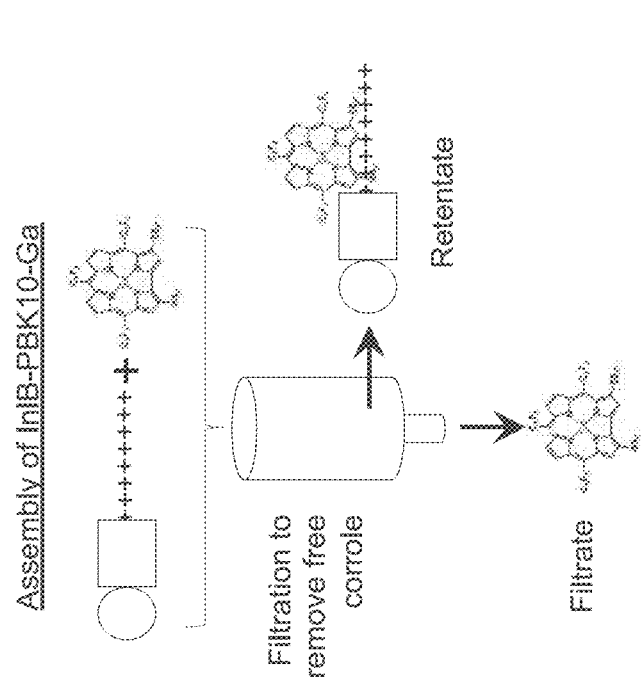
Figure 9C:
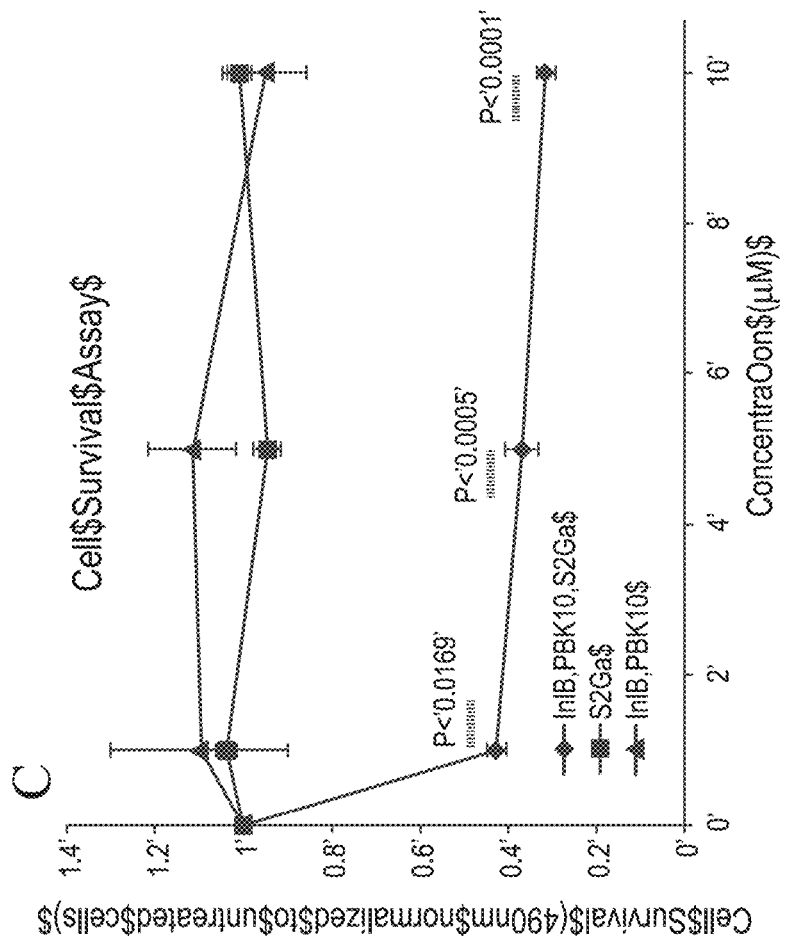
Figure 9B:
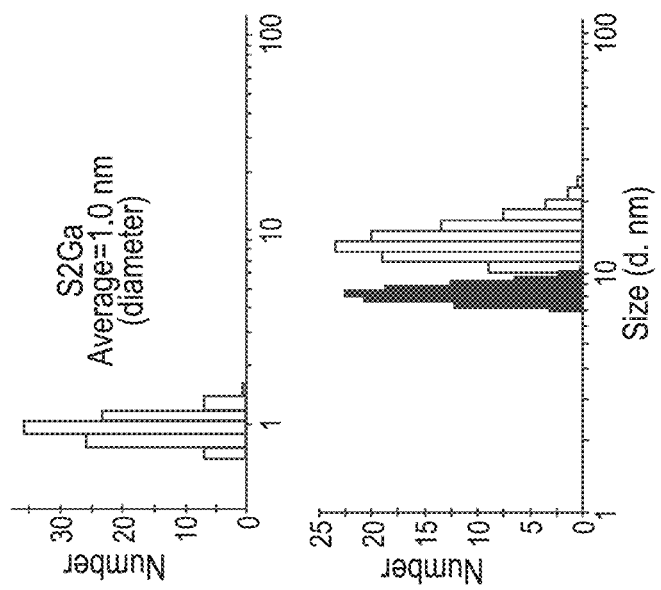

For this study, InlB-PBK10 was mixed with the Ga-corrole to promote non-covalent assembly, and the resulting InlB-PBK10-Ga complex characterized by transmission electron microscopy (TEM) and dynamic light scattering (FIGS. 9A, and 9B). TEM (right panels of FIG. 9A) shows the spherical assemblies formed when Ga-corrole (+S2Ga) is added to InlB-PBK10 compared to InlB-PBK10 alone (−S2Ga). The imaging shows that the protein and corrole form 10-20 nm diameter clusters. Dynamic light scattering, used to measure particle size, shows that InlB-PBK10 alone forms particles of 8.4 nm average diameter while InlBPBK10-Ga is about 16.4 nm diameter.

To examine whether InlB-PBK10-Ga could penetrate cells and induce corrole-mediated toxicity in c-MET positive cancer cell lines, we exposed MDA-MB-435 cells to 1 µM, 5 µM and 10 µM of each of the following: InlB-PBK10, S2Ga and InlB-PBK10-Ga. At 1 µM concentration, InlB-PBK10-Ga reduced cell survival by 60% whereas 1 µM and higher concentrations of S2Ga alone and InlB-PBK10 alone did not affect cell survival. These data affirm that InlB-PBK10 bears endosomolytic capacity, and shows that this construct is capable of delivering cytotoxic agents such as Ga-corroles into cells expressing cell surface c-MET (FIG. 9C).

Figure 9E:
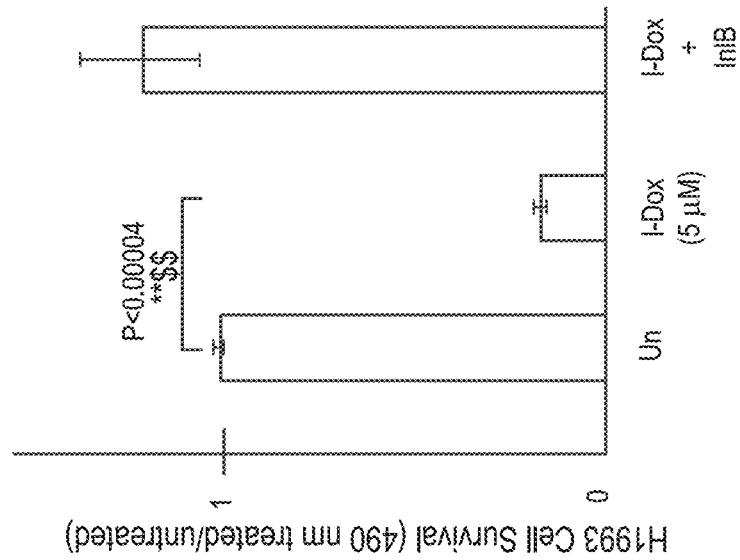
Figure 9D:
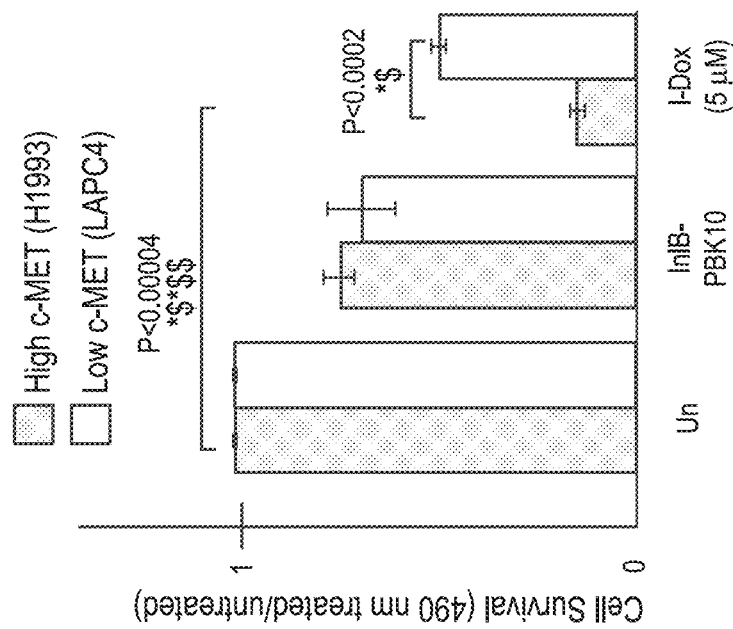

To further evaluate the therapeutic capacity of InlB-PBK10, it was assessed whether this protein could be used to deliver more mainstream chemotherapeutic molecules. Doxorubicin (Dox) is an FDA approved cytotoxic agent that is used for a broad range of cancer types. If such drugs could be targeted mainly to tumor cells, it would be beneficial in terms of reducing side effects. In this approach, first Dox is intercalated into a double stranded oligo to form DNA-Dox, which then can bind to the polylysine of InlB-PBK10 (via charge interactions with the DNA phosphate backbone) and form a complex that we have designated, I-Dox. The I-Dox complex (5 µM with respect to Dox concentration) was incubated on the indicated cell lines under the conditions described in the Methods. InlB-PBK10 was incubated at equivalent concentrations to that in the I-Dox complex. Cell survival was assessed by metabolic (MTT) assay at 24 h after treatment. The I-Dox complex induced significant toxicity to cells with high c-MET expression (H1993) when compared to cells with low c-MET expression (LAPC4) (FIG. 9D). H1993 cells were first treated with free InlB ligand to block c-MET, followed by exposure to I-Dox at the same conditions as above. InlB-PBK10 alone appeared to slightly but not significantly reduce cell numbers, suggesting that the main mechanism of cell death was through the delivery of Dox. Additionally, free InlB ligand inhibited cytotoxicity by I-Dox, suggesting that I-Dox-mediated cytotoxicity occurs through c-MET binding and entry for the delivery of Dox (FIG. 9E).

Experimental Procedures

Cells.

Human breast cancer cell lines (MDA-MB-435* and MDA-MB-231) were obtained from the National Cancer Institute. Human lung cancer (H1993), and African Green Monkey Kidney Fibroblast (Cos-7) cell lines were obtained from ATCC. Human ovarian cancer cells (A2780) were obtained from Sigma-Aldrich. Prostate cancer lines (LNCaP$^{Neo/RANKL}$, LNCaP$^{Neo}$) were kindly provided by Dr. Leland Chung (Cedars-Sinai Medical Center). MDA-MB-435 and MDA-MB-231 were maintained in DMEM, 10% v/v fetal bovine serum (FBS, Sigma-Aldrich), and 1% v/v penicillin/streptomycin (Sigma-Aldrich) under 5% $CO_2$. H1993 and A2780 cells were maintained in RPMI, 10% v/v FBS, and 1% v/v penicillin/streptomycin under 5% $CO_2$. Cos-7 cells were maintained in DMEM/F12 medium, 20% v/v non-heat inactivated fetal bovine serum (ATCC 30-2020), and 1% v/v penicillin/streptomycin (Sigma-Aldrich) under 5% $CO_2$. LNCaP$^{Neo/RANKL}$, LNCaP$^{Neo}$ were maintained in RPMI medium, 10% v/v FBS, and 1% v/v penicillin/streptomycin and 200 µg of G418 disulfate salt solution (Sigma Aldrich G8168). 200 µg/ml of hygromycin (GEMINI Bio-products 400-123) was added to the medium of the LNCaP$^{Neo/RANKL}$ cells to maintain the RANKL-expression plasmid. In order to maintain equivalent confluency between the cell lines, in certain assays they were plated according to their growth rate.

DNA Constructs.

The targeting construct, InlB-PBK10, was produced by a two-step cloning method (Summarized in FIG. 8A) in which sequences encoding InlB and PBK10 were sequentially ligated together into the protein expression plasmid, pRSET-A (Invitrogen, Carlsbad, Calif., USA). A plasmid construct encoding aa 36-321 of internalin B (pMET-30-InlB321) (CeBiTec), Bielefeld University, Germany) was used as a template for polymerase chain reaction (PCR) amplification using forward and reverse oligonucleotide primers containing the sequences, 5'-AGTGAGCTCGA-GACTATCACTGTG-3' (SEQ ID NO:1) and 5'-GTTGGTGACTTTCTCCCACCTTCACCACCTT-CATCTAGATATCCATGGTAT-3' (SEQ ID NO:2) respectively. A SacI restriction site was introduced in the forward primer for in-frame insertion into pRSET-A. BglII and KpnI restriction sites were introduced into the reverse primer for subsequent in-frame insertion of PBK10 just 3' to the InlB coding sequence. The reverse primer also contains a sequence encoding a flexible linker (GlyGlySerGlyGlySer) (SEQ ID NO:3) in-between the InlB and PBK10 sequences. The 800 bp InlB PCR product was digested with SacI and KpnI for ligation into pRSET-A. The resulting construct, pRSETA-InlB, was then digested with BglII and HindIII to accommodate the insertion of PBK10 in-frame with InlB. PBK10 was excised from the plasmid, pRSET-PBK10, using BamHI and HindIII restriction enzymes, and inserted into the BglII-HindIII sites of pRSETA-InlB, resulting in the pRSET-InlB-PBK10 construct.

The pRSETA-GFP-InlB construct that encodes InlB321 as a carboxy [C]-terminal fusion to green fluorescent protein (GFP) was made by digesting the 800 bp InlB PCR product, described earlier, with SacI and BglII, and ligating this into the pRSETA-GFP plasmid for in-frame cloning of InlB321.

Protein Expression and Purification from Bacteria.

Overnight cultures of BLR(DE3)pLysS (Novagen, Madison, Wis., USA) bacterial transformants were inoculated 1:50 in LB containing 0.5 mg/ml ampicillin and 0.034 mg/ml chloramphenicol, and 0.0125 mg/ml tetracycline. When cultures reached an absorbance reading of 0.6 at an optical density wavelength of 600 nm (OD 600), cultures were induced with 0.4 mM IPTG and grown for a further 3 h at 37° C. with shaking. Cultures were harvested and pelleted. Cell pellets were resuspended in lysis buffer (50 mM Tris, pH 8.0, 50 mM NaCl, 2 mM EDTA, pH 8.0) and lysed by addition of 0.1% Triton X-100 and one cycle of freeze-thawing, with 1 mM phenylmethylsulfonyl fluoride (PMSF) added during the thaw. After thawing, lysates received 10 mM $MgCl_2$, and 0.01 mg/ml DNase and lysates were rocked for 10 minutes at room temperature to allow digestion of genomic DNA before lysates were returned to ice, after which they received 300 mM NaCl and 10 mM imidazole. Lysates were transferred to pre-cooled centrifuge tubes, balanced, and centrifuged at 4° C. in a pre-chilled rotor at 39,000×g for 1 hour. Supernatants were recovered, added to Ni-NTA resin (Qiagen, Valencia, Calif., USA) pre-equilibrated with MCAC-10 (50 mM $NaH_2PO_4$, 300 mM NaCl, 10 mM imidazole, and 0.1% Triton X-100, pH 8.0), and incubated for 1 h on ice. The resin containing bound protein was washed with 20 mL of MCAC-10 buffer one time for 10 minutes rocking on ice and three times with MCAC-20 (50 mM $NaH_2PO_4$, 500 mM NaCl, 20 mM imidazole, and 10% glycerol, pH 8.0), followed by elution with 2 mL of a solution of 50 mM Na-phosphate, pH 8.0, 300 mM NaCl, 250 mM imidazole, and 10% glycerol. Proteins were simultaneously buffer exchanged into low-salt buffer and concentrated by ultrafiltration (Amicon Ultra Centrifugal Filters—Ultracel—50K (Millipore, Bedford, Mass., USA) and their concentrations measured using the BioRad protein quantification assay (BioRad Laboratories, Hercules, Calif., USA).

Protein Detection.

Denaturing polyacrylamide gel electrophoresis was performed in a discontinuous gel buffer system as known in the art. Proteins were electrically transferred on to nitrocellulose using 192 mM glycine, 25 mM Tris, and 20% methanol in a BioRad semi-dry transfer cell set at constant voltage (20 V) for 40 min. Blots were blocked with 3% bovine serum albumin in Tris-buffered saline (10 mM Tris, pH 7.5, 150 mM NaCl). Blots were incubated overnight with anti-RGS-His Tag antisera (Qiagen) at a 1:1500 dilution in blocking buffer. Antibody—antigen complexes were detected by incubation with horseradish peroxidase (HRP) conjugated secondary antibodies (Sigma, St Louis, Mo., USA), followed by reaction with HRP substrate and chemiluminescence detection reagents (Thermo Fisher), and exposure to film (Hyperfilm ECL; Amersham Pharmacia Biotech).

ELISA Based Assay for c-MET Cell Surface Expression.

To determine c-MET levels on cell lines, cells were plated in 96-well plates using the following cell numbers: $8 \times 10^3$ MDA-MB-231, MDA-MB-435, A2780, LNCaP$^{Neo/RANKL}$, LNCaP$^{Neo}$ and $9 \times 10^3$ for H1993 and LAPC4 per well. 48 Hrs later media was aspirated and cells were briefly washed with phosphate-buffered saline (PBS) containing 1 mM $MgCl_2$ and 1 mM $CaCl_2$ (PBS+), then fixed in 4% PFA in PBS for 12 min at room temperature (RT), followed by 3 washed with PBS+(200 μL per well) before a 1 hr incubation in blocking solution (3% BSA/PBS, 100 μL per well) at RT. Anti-c-MET antibody (mouse monoclonal anti-c-MET used at 0.87 μg/mL; Dr. Knudson) was added in triplicate wells (100 μL per well) and incubated for 1 hr at RT. Cells were washed three times with PBS+ and incubated for 1 hr at RT with HRP-conjugated secondary antibody at a 1:2000 dilution. Cells were washed 3 times with PBS+ and once with distilled water, and 100 μL of TMB (eBioscience) solution was added to each well, according to manufacturer's instructions. The plates were incubated with substrate for 30 min (or until the blue color development was visible) in the dark, and the reaction was stopped by adding 100 μL of 1N HCl. Absorbance were measured at 450 nm in a Spectra MaxM2 plate reader (Molecular Devices Corp.) A crystal violet assay was then performed to determine relative cell number. Briefly, cells were washed once with PBS+ (2004/well) and incubated with 0.1% crystal violet (100 μL/well) for 15 minutes at RT. Cells were thoroughly washed 4 times with PBS+ (200 μL/well) and incubated with 95% Ethanol (100 μL/well) for 10 minutes at RT. Absorbances were measured at 490 nm.

Cell Binding Assay.

To determine the binding of different concentrations of InlB-PBK10 to cells, cells were plated in 96-well plates at the following concentrations: $8 \times 10^3$ LNCap$^{Neo/RANKL}$, LNcap$^{Neo}$ and $9 \times 10^3$ for H1993 and LAPC4 per well. At 48 hrs later, media was aspirated and cells were briefly washed with 100 μL Buffer A (serum free DMEM, 20 mM HEPES pH 7.4, 2 mM $MgCl_2$, 3% BSA). Cells were incubated with 50 μL of buffer A containing the indicated concentrations of InlB-PBK10 for 1 hour on ice with agitation at 4° C. The cells were washed with PBS+(200 μL/well) one time and subject to cell surface ELISA as described earlier (cell surface expression ELISA for c-MET), with the following modifications: To detect InlB-PBK10, plates were incubated overnight with primary antibody (RGS-His; Qiagen) at 1:1500 dilution, and one hour at room temperature with secondary antibody (goat anti mouse, at 1:2000 dilution).

For competitive inhibition assays, the indicated concentrations of InlB were incubated on cells before adding InlB-PBK10. Specifically, cell lines plated as described earlier were briefly washed with 1004 Buffer A, followed by incubation in 50 μL of buffer A containing 1 μM, 5 μM or 10 μM of InlB for an hour on ice with agitation at 4° C. Cells were washed one time with Buffer A (100 μL/well) and then incubated with 50 μL of Buffer A containing 1 μM of InlB-PBK10 for an hour on ice with agitation at 4° C. The cells were washed with PBS+(200 μl/well) one time and processed for immune-detection of surface-bound InlB-PBK10 as described earlier, except plates were incubated with an antibody that recognizes the penton base domain of InlB-PBK10 (Ad5 antibody; Abcam) at 1:5000 dilution. Plates were incubated with secondary antibody (goat anti rabbit, at 1:2000 dilution), for one hour at room temperature. Binding was detected as explained earlier for c-MET cell surface expression ELISA.

Cell Survival Assay.

MDA-MB-435 cells were plated in 96-well plates at $8 \times 10^3$ cells per well. 48 hrs later medium was aspirated and the cells were incubated with 30-50 μl of media containing the different concentrations of InlB-PBK10-Ga and S2Ga (1, 5 and 10 μM) for 4 hours on a rocker at 37° C. in a 5% $CO_2$ incubator. After the 4 hour incubation period, additional media was added to bring the total volume per well to 100 μL and cells were incubated for approximately 24 hrs without rocking. Promega CellTiter 96 Aqueous Non-Radioactive Cell Proliferation Assay was used to measure cell viability. Medium was removed and 100 μl fresh media was added to the wells. Per manufactures' instructions, 2.0 mL of MTS solution was mixed with 100 μL of PMS solution and 20 μL was added to each well. Plates were incubated at 37° C. with 5% $CO_2$ and absorbance was read at 490 nm at 1 and 2 hours after the addition of the MTT reagents. Crystal violet staining was then performed to determine the relative cell number. Briefly, cells were washed with PBS+, containing 1 mM $Ca^{2+}$ and 1 mM $Mg^{2+}$, then incubated with 0.1% crystal violet (100 μl/well) for 15 minutes at RT and then washed 4 times with PBS+(200 μL/well). Plates were incubated with 95% Ethanol (100 μL/well) for 10 min. at RT, and absorbance was measured at 590 nm.

InlB-PBK10 Uptake/Intracellular Trafficking Assays.

For InlB-PBK10 uptake assays, cells were plated on coverslips in a twelve-well dish at $1 \times 10^5$ cells/well and grown for 2 days. On the day of treatment, dishes were transferred on ice and the cells were treated for the indicated experiments according to the following methods. To study the time course of uptake, cells were washed twice with cold PBS, and then 0.4 mL of Buffer A with 8 μg of InlB-PBK10 was added to each well. Dishes were incubated for 1 h on ice rocking at 4° C. to promote receptor binding but not internalization, and then cells were washed with cold PBS to remove unbound protein. Wells then received pre-warmed complete media, and dishes were incubated at 37° C. at 5% $CO_2$ for the indicated time points. The individual coverslips were then removed, washed three times with PBS/1% $MgCl_2$ then fixed with 4% paraformaldehyde in PBS for 15 min at room temperature. Coverslips were washed three times with PBS, then incubated with 50 mM ammonium chloride in PBS for 5 min, 0.1% Triton X-100 in PBS for 5 min and then blocked with 1% BSA in PBS for 30 minutes at room temperature. Cells on coverslips were incubated with primary antibodies overnight at 4° C., washed three times with PBS and incubated with secondary antibodies for 1 h at room temperature in the dark. Where indicated, cells counterstained for actin and nuclei were incubated with Texas Red x-Phalloidin (Invitrogen T7471) at 1:100 dilution during the secondary antibody incubation, followed by a 5 min incubation in DAPI at 300 nM final concentration. Phalloidin, DAPI and primary and secondary antibodies were all diluted in 1% BSA in PBS. After secondary antibody and DAPI treatment, cells on cover slips were washed three times with PBS and mounted in Prolong Antifade mounting medium (Molecular Probes, Eugene, Oreg., USA). For detecting InlB-PBK10 the RGS-His antibody (Qiagen) was used at 1:150 dilution and a fluorophore-conjugated goat anti-mouse (FITC-conjugated) at dilution of 1:500 was used for fluorescence detection at 488 nm for InlB-PBK10, 405 nm (DAPI) for nuclei and 532 nm (Texas red) for F-Actin.

InlB-PBK10-Dox (I-Dox) Assembly.

The viral capsid-derived fusion protein, InlB-PBK10, was assembled with doxorubicin following well-established procedures. Briefly, complementary oligonucleotide duplexes were prepared by mixing together with equal molar concentration of the 30 base oligonucleotide, LLAA-5 (5'-CGCCT-GAGCAACGCGGCGGGCATCCGCAAG-3') (SEQ ID NO:4) and its corresponding reverse complement, LLAA-3. The mixture was boiled for 5 minutes and cool down to room temperature for 30 min to promote annealing of oligonucleotides. The double stranded oligos were mixed with Dox at 1:10 molar ratio (DNA:Dox) and incubated at room temperature (RT) for 30 minutes, followed by incubation with InlB-PBK10 at 6:1 molar ratio of InlB-PBK10: DNA-Dox in HBS, and ultrafiltration using 50 k MW cutoff (mwco) filter membranes (which was prepared by pre-incubating with 10% glycerol for 2 hours-overnight) to isolate I-Dox from incompletely assembled components. The complexes were centrifuged at 4000×g for 15 min or until volume was reduced by ≥80%. The Dox concentration in I-Dox was determined by extrapolating the measured absorbance at 480 nm or fluorescence at 590 nm (Ex: 480 nm) against a Dox absorbance or fluorescence calibration curve (SpectraMax, Molecular Devices, USA). The concentration of Dox was calculated by applying the Beer-Lambert equation: (Absorbance at λmax/Dox extinction coefficient)× dilution factor=concentration (M), using a Dox coefficient of 11, 500 $M^{-1}$ $cm^{-1}$. The I-Dox doses used in experiments is based on the concentration of Dox in I-Dox.

InlB-PBK10-Ga assembly.

InlB-PBK10 was Noncovalently Assembled with sulfonated gallium corrole (S2Ga) by incubating a 10× molar excess of corrole with InlB-PBK10 in the dark at 4° C. for 1 h with gently agitation. The unbound corroles were removed by ultrafiltration through 50 K MW cutoff spin column filters (Millipore Corporation, Billerica, Mass., USA) according to the manufacturer's procedures for filtration, and the complexes washed with PBS until the filtrate clarified. The retentates retained their bright green color (indicative of corrole pigment) throughout the filtration process. The retentates were resuspended in PBS and measured for absorbance at the $\lambda_{max}$ of the corrole to obtain the corrole concentration as described earlier. Whereas the $\lambda_{max}$ of S2Ga, for example, shifts from 424 to 429 nm when bound to proteins, this does not dramatically change the estimation of corrole concentration in complexes.

FACS Analysis.

To evaluate binding of InlB321, H1993 and Ln GFP cells were cultured for 48 hrs. After washing two times with PBS, the cells were detached by incubating in 2 mM EDTA for 5-10 min at 37 C. PBS containing 0.01% $MgCl_2$ and $CaCl_2$ (0.01% PBS+) was added to the cells and spun for 4 min at 2000 rpm. Cells were washed with 0.01% PBS+ three more times, resuspended, counted, and divided into the Eppendorf tubes. The tubes were spun for 2 minutes at 300×g and resuspended with 3% milk in PBS containing the indicated concentrations of InlB and incubated on ice in the cold room for 1 hr. Cells were then washed four times with PBS and incubated with RGS-His antibody diluted 150 fold in 3% BSA in PBS for 30 min at room temperature. Cells were washed four times before re-suspending them with secondary antibody antibody, Alexa Fluor 647 Goat Anti-Mouse IgG (H+L), in 3% BSA and incubated at room temperature for 30 min. Cells were washed 4 times, incubated with 0.1% PFA for 15 min and then washed again for four times and analyzed with Beckman Coulter Cyan ADP FACS machine.

To verify that cell binding by InlB321 is through c-MET, InlB321 and MET peptide (YCP2247 SPEED BioSystems. Rockville, Md.) were incubated in 3% milk in 1×PBS for 30-40 min on ice before binding to cells. The binding assay was performed as described above.

Cell Pull Down Assay.

MDA-MB-435 cells grown for 48 hrs were lifted using 2 mM EDTA in 1×PBS at 37° C. with agitation for 5-10 min. After spinning the cells for 5 min at 300×g, they were washed once and resuspended in Buffer A+3% BSA and divided into four Eppendorf tubes ($2 \times 10^6$ cells/tube). The cells were spun again and resuspended into 500 µL of buffer A+3% BSA. In three of the tubes 0.4 µM, 2 µM and 4 µM of InlB was added and no protein was added to the fourth tube; all tubes were incubated on ice for 1 hr. Following washing and spinning of all cells to remove unbound InlB, 0.4 µM of InlB-PBK10 in 500 µL of Buffer A was added to all four tubes, followed by rocking on ice for 2 hours to promote receptor binding but not internalization. Cells were washed and spun three times as described earlier. Pellets then suspended in 50 µL of SDS-PAGE sample buffer and evaluated by SDS-PAGE/Western blotting using an antibody specific to InlB-PBK10 (Ad5 antibody, which recognizes the penton base) at the 1:5000 dilution.

Example 3: Inl-PBK10 Biodistribution in Nu/Nu Mice Bearing Bilateral Flank MDA-MB-435 Tumors

BACKGROUND

As shown in the previous example entitled "A Protein Nano-Construct Targeted to c-Met", FIG. 6, MDA-MB-435 cells display marked levels of c-MET on the cell surface. Moreover, as shown in FIG. 7E, the c-MET targeted protein construct, InlB-PBK10, binds these cells through an interaction that is competitively inhibited by the c-MET ligand, InlB, indicating that this construct can bind these cells through c-MET. FIG. 8 shows that InlB-BK10 enters these cells after receptor binding, and FIG. 9C shows that the protein can mediate the delivery of a membrane impermeable toxic molecule (gallium-metallated corrole) into these cells, causing cell death (thus also verifying that Inl-PBK10 is capable of endosomal membrane disruption).

Results

Figures 10A, 10B:
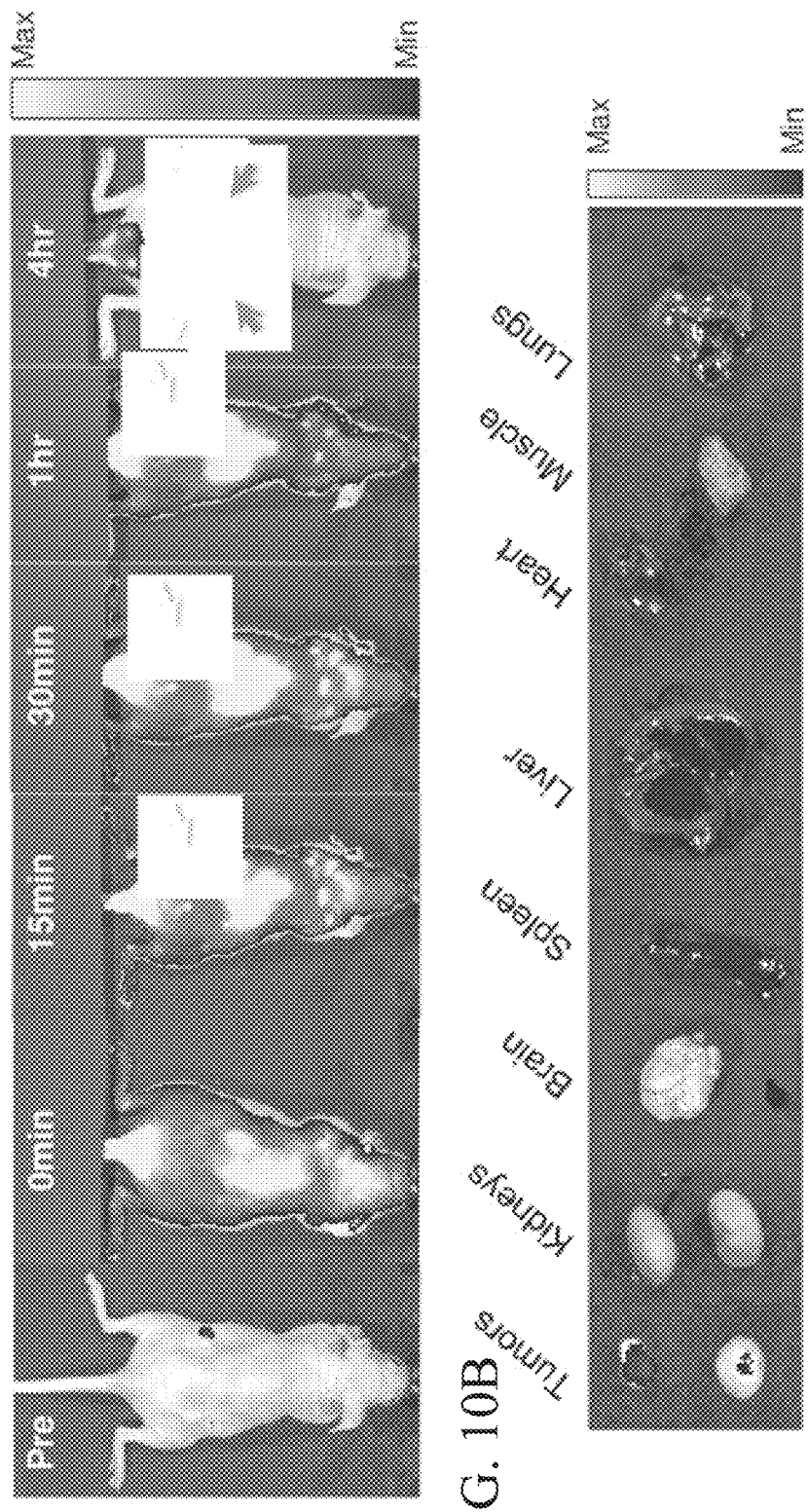
FIGS. 10A-10B show a Xenogen Spectrum image for the biodistribution of InlB-PBK10 after systemic (tail vein) delivery in a nu/nu mouse bearing subcutaneous bilateral flank MDA-MB-435 tumors.

Here we evaluated the biodistribution of Inl-PBK10 in a mouse with MDA-MB-435 tumors to assess whether it is capable of accumulating at these tumors in vivo. To do so, a female nu/nu mouse bearing bilateral flank xenografts of MDA-MB-435 tumors received a single tail vein injection of Alexa680-labeled InlB-PBK10 (2 nmol protein) and was imaged by Xenogen imaging at the indicated time points after injection, using 640 nm excitation and 700 nm emission filters. Whole animal imaging shows considerable clearance of fluorescence from the animal by 4 h after injection (FIG. 10A). After the 4 h time point, the mouse was sacrificed and tumors and tissues removed for further imaging. While the tumors show some fluorescence accumulation, a significant proportion of injected material was eliminated to the kidney by 4 hours while some fluorescence could be detectable in the liver (FIG. 10B). Remaining tissues, including heart, spleen, lung, brain, and skeletal muscle, showed no detectable fluorescence (FIG. 10B). Further studies will entail tissue harvest at earlier and later time points to determine whether delivery to the kidney is the result of rapid elimination, as well as determining biodistribution with a competitive inhibitor to verify that tumor delivery occurs via c-MET.

Example 4: Nanobiologic Targeting of Brain Metastatic Breast Tumors

Elevated cell surface levels of the human epidermal growth factor receptor subunit 3 (HER3) is associated with metastatic breast tumors, including those that spread to the brain. Whereas a number of targeted therapies are currently used to combat peripheral breast tumors, the delivery of these molecules to brain metastases is limited by the blood brain barrier (BBB). This is exemplified by HER2+ breast tumors that metastasize to the brain: these tumors, while targetable outside of the central nervous system (CNS) by HER2 antibodies such as trastuzumab, are unreachable by these same antibodies because the HER2 subunit, though present on the brain endothelium, does not mediate antibody transcytosis across the blood vessel wall.

HER3, on the other hand, undergoes rapid transcytosis across the brain endothelium upon ligand binding, which normally occurs to mediate the delivery of neuregulin growth factors for neural growth and maintenance. We have developed a self-assembling nanobiological particle, HerMn, which uses HER3 as a portal for targeted entry of toxic molecules into tumor cells. HerMn is a 10-20 nm diameter serum-stable particle comprised of the receptor-targeted cell penetration protein, HerPBK10, non-covalently assembled with a sulfonated manganese(III) corrole (S2Mn or Mn-corrole) (FIG. 11). The targeting domain of HerPBK10 is derived from the ligand, heregulin alpha, which specifically interacts with the human epidermal growth factor receptor subunit 3 (HER3) and induces rapid receptor-mediated endocytosis. As HER3 is the preferred dimerization partner of HER2, and HER2-3 heterodimers are prevalent on HER2+ tumor cells, we have previously shown that HerPBK10 can target therapeutic and imaging molecules to HER2+ tumors in mice, mediating tumor growth ablation at >10× lower dose compared to the chemotherapy agent, doxorubicin, while sparing heart and liver tissue, and with no detectable immunogenicity. Tumor-targeted toxicity by HerMn occurs by mitochondria membrane disruption and superoxide-mediated damage to the cytoskeleton. HerMn can also elicit tumor-selective detection by magnetic resonance imaging (MRI) due to the paramagnetic property of the corrole.

HerMn appears to distribute to the brain after systemic injection in mice, in addition to showing preferential homing and toxicity to subcutaneous HER2+ tumors. Interestingly, the Mn corrole is known to exhibit neuroprotective effects due to its antioxidant activity on normal tissue. In support, HerMn supports human cardiac cell survival ex vivo. Taken altogether, it is intriguing to speculate that HerMn may have the capacity to target toxicity to brain-metastatic breast tumors while sparing off-target tissue due to both its targeting capacity and ability to provide beneficial protective effects to normal tissue such as the brain and heart.

Background

Brain Metastasis is a Serious Clinical Problem.

Patients with breast cancer metastases to the brain on average survive less than one year. While a growing repertoire of targeted therapies have emerged for treating peripheral tumors, most are unsuitable for treating brain metastases due to their inability to cross the blood brain barrier (BBB). An example of this is the use of the monoclonal antibody, trastuzumab (Tz), which is directed against the human epidermal growth factor receptor subunit 2 (HER2) for treating HER2+ breast cancer. HER2+ cancers are associated with aggressive tumors, recalcitrance to standard therapies, metastasis, and increased mortality. HER2+ tumors that metastasize to the brain cannot be treated with Tz because HER2, though present on the brain endothelium, does not transcytose across the blood vessel wall. Triple-negative breast cancer (TNBC), which is HER2- and also brain-metastatic, has even fewer options due to the lack of specific cell surface biomarkers. While lapatinib (Lp), a small molecule tyrosine kinase inhibitor (TKI) of HER2 and EGFR, can readily permeate the cell membrane to target both tumor types, these tumors are likely to resist such inhibitors due in part to elevation of HER3.

Results

HerPBK10 is Specific to HER3.

HerPBK10 contains the receptor binding region of the HER3 ligand, heregulin-α (amino acids 35-239, comprising the Ig-like and EGF-like domains), fused to a membrane-penetrating moiety derived from the adenovirus penton base capsid protein (FIG. 11A). HerPBK10 was originally designed as a non-viral gene transfer vector, containing payload assembly, targeting, internalization, and endosomal penetration functions within a single multidomain protein molecule. As HER3 is the preferred dimerization partner of HER2, and HER2–3 heterodimers are prevalent on HER2+ tumor cells, it has been shown that HerPBK10 can target therapeutic and imaging molecules to HER2+ tumors in mice, mediating tumor growth ablation at >10× lower dose compared to the chemotherapy agent, doxorubicin, while sparing heart and liver tissue, and with no detectable immunogenicity.

The specificity of HerPBK10 to HER3 is supported by its ability to bind to an immobilized peptide containing the extracellular domain of human HER3 (FIG. 12A). This is inhibited by pre-adsorption of HerPBK10 with free HER3 peptide in vitro (FIG. 12A). The same peptide also inhibits binding to both human (FIG. 12B) and mouse (FIG. 13B-C) HER3+ cells. Notably, the ligand-binding domain of mouse and human HER3 share high (94%) sequence identity (FIG. 13A). While HER2–3 heterodimers are prevalent on HER2+ tumor cells, the heterodimerization-inhibiting antibody, pertuzumab (Pz), does not prevent HerPBK10 binding to cellular HER3 (FIG. 12B), indicating that HER2–3 dimerization is not required for HerPBK10 binding. Binding is also not inhibited by a HER4 peptide or betacellulin (which blocks HER4) (FIG. 12B), indicating that HerPBK10 is HER3-specific.

Sera from HER2+ patients and age-matched controls do not prevent HerPBK10 binding to HER2+ cells in culture (and show no significant differences between one another), in contrast to the addition of excess recombinant ligand (+Her) used as a competitive inhibitor (FIG. 12C). Previous studies have shown that repeat dosing of HerPBK10 in immune-competent mice do not produce detectable neutralizing antibody formation against the protein. Moreover, polyclonal antibodies generated against whole adenovirus that can recognize HerPBK10 do not prevent receptor binding to cells in culture.

HerPBK10 Self-Assembles with Mn-Corroles to Form HerMn Nanoparticles.

The carboxy [C]-terminus of HerPBK10 is comprised of a decalysine tail (FIG. 11A), which can mediate electrophilic binding to anionic molecules, including corroles. Corroles are macrocyclic molecules with structural similarity to porphyrins and likewise can contain a metal ligand (FIG. 11B). Sulfonated corroles are amphiphilic, soluble in physiological solutions, and can spontaneously bind proteins through non-covalent interactions, including electrophilic and hydrophobic interactions. The anionic sulfonato groups prevent non-specific cell entry due to repulsion by the negatively charged cell membrane, thus enabling the potential to direct corrole delivery into target cells via a carrier protein. We have combined HerPBK10 with a sulfonated manganeses(III) corrole (S2Mn or Mn-corrole) to form rapidly self-assembling 10-20 nm diameter particles designated HerMn (FIG. 11C-D). These particles contain multiple corrole molecules bound to a single protein (25-35 corroles/protein), and can withstand high-speed ultrafiltration. These findings are consistent with our previous studies and those of our collaborator showing that corroles can bind in protein pockets with negligible dissociation, and once bound to HerPBK10, resist transfer to serum proteins.

HerMn Targets HER3+ Tumors.

Figure 14:
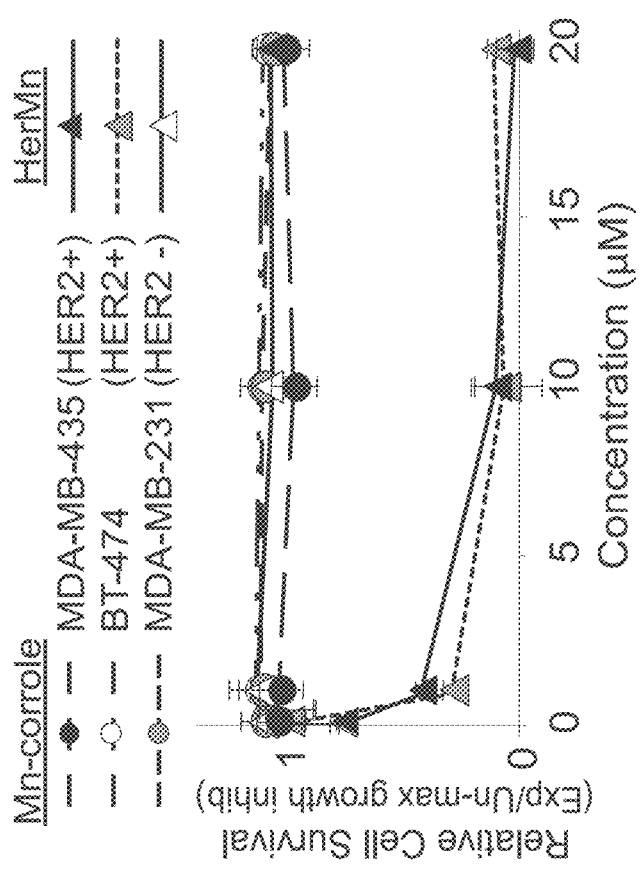
FIG. 14 is a graph showing the data for HerMn toxicity on human HER2+ and HER2-tumor cells.

HerMn exhibits targeted toxicity to HER2+/HER3+ but not HER2-/HER3-tumor cells in culture while Mn-corrole has no effect on cell survival. The data is shown in FIG. 14, where each cell line received the indicated concentration of HerMn or S2Mn and was assessed for survival 24 hours later via crystal violet (CV) stain. N=3 per concentrate, from 3 separate experiments. It has been shown that the targeting ligand of HerPBK10 induces rapid endocytosis after receptor binding. As sulfonated corroles are unable to breach the endosomal membrane on their own, the penton base moiety of HerPBK10 enables effective membrane disruption after endocytic uptake, and entry into the cytoplasm.

Figure 15A:
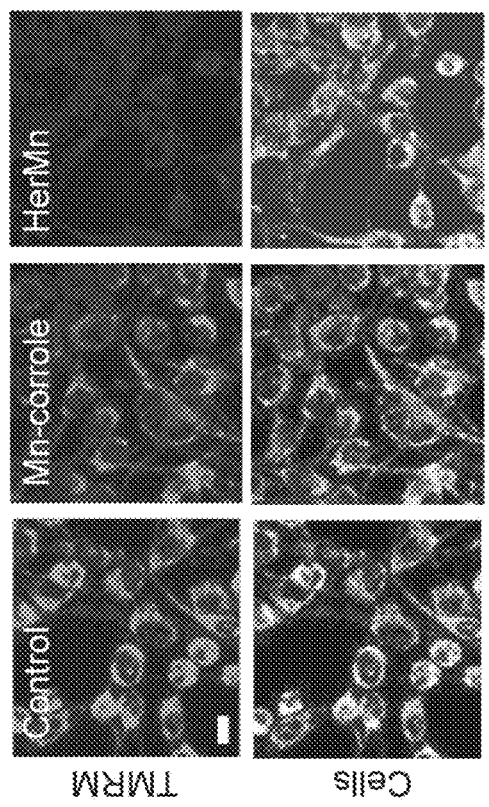
FIGS. 15A-15B are photographs showing the mechanism of HerMn cytotoxicity.
Figure 15B:
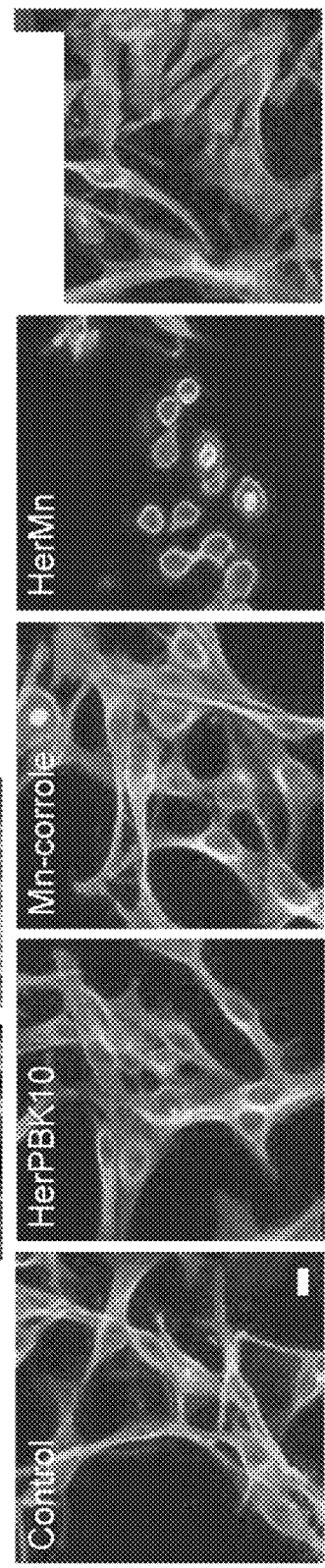

In one experiment, cells received 10 μM S2Mn or HerMn, then TMRM (30 nM) in HBSS 24 hours later. The results are shown in FIG. 15A, where the control is PBS-treated. Confocal fluorescence images, FIG. 15B, show superoxide-mediated collapse of actin (red) and tubulin (green) by HerMn (5 μM) after 24 h incubation on MDA-MB-435 cells. S2Mn (5 μM), HerPBK10 (at equivalent protein concentration as HerMn) and PBS served as controls. Additional cells received Tiron (5 mM) for 1 h before HerMn treatment. Blue, nucleus. Scale bar=10 μm Once in the cytoplasm, HerMn collapses mitochondrial membrane potential (FIG. 15A) and the cytoskeleton through superoxide elevation and oxidative damage to these structures (FIG. 15B), consistent with gallium(III) corrole (S2Ga or Ga-corrole).

It is discovered that Ga-corrole directly binds the mitochondrial outer membrane protein, TSPO. The results are shown in FIG. 16. Soluble recombinant TSPO protein was incubated with S2Ga at equivalent molar concentrations (1 μM) for ~20 min at room temp followed by ultrafiltration to remove free, unbound S2Ga. Retentates were evaluated for the presence of TSPO protein-bound corrole by measuring the absorbance and fluorescence spectra. Where indicated, PK11195 was used as a competitive inhibitor for the porphyrin-binding site on TSPO (FIG. 16A-B). There is evidence of HerGa interaction with TSPO in situ. MDA-MB-435 cells were transfected with a plasmid expressing exogenous TSPO (as a competitive inhibitor of endogenous TSPO binding) 24 h before cells were treated with HerGa and examined for HerGa-mediated mitochondrial disruption, evidenced by reduced red fluorescent dye accumulation in mitochondria and accumulated green fluorescence in the cytoplasm (FIG. 16C-D).

TSPO translocates porphyrins and other metabolites into mitochondria for processing, interacts with components of the mitochondrial permeability transition pore complex, and contributes to cellular homeostasis. Ga-corrole specifically recognizes the porphyrin-binding site on TSPO (FIG. 16A-B), as corrole binding can be competitively inhibited by PK11195, which inhibits porphyrin binding to TSPO. Overexpression of recombinant soluble TSPO in MDA-MB-435 cells prevents corrole-mediated disruption of mitochondrial membrane potential (FIG. 16C-D), suggesting that the corrole interacts with TSPO in situ. As the Mn-corrole exhibits similar mitochondrial membrane disruption as the Ga-corrole, it is likely that TSPO is a molecular target of Mn-corrole. In a xenograft mouse tumor model, HerMn homes to tumors in vivo after systemic delivery, bypassing most normal tissue including the heart (FIG. 17), and ablates tumor growth at very low pharmacologic dose (0.008 mg/kg) (FIG. 18A). The Mn-corrole is also paramagnetic, thus useful for MRI.

Figure 17:
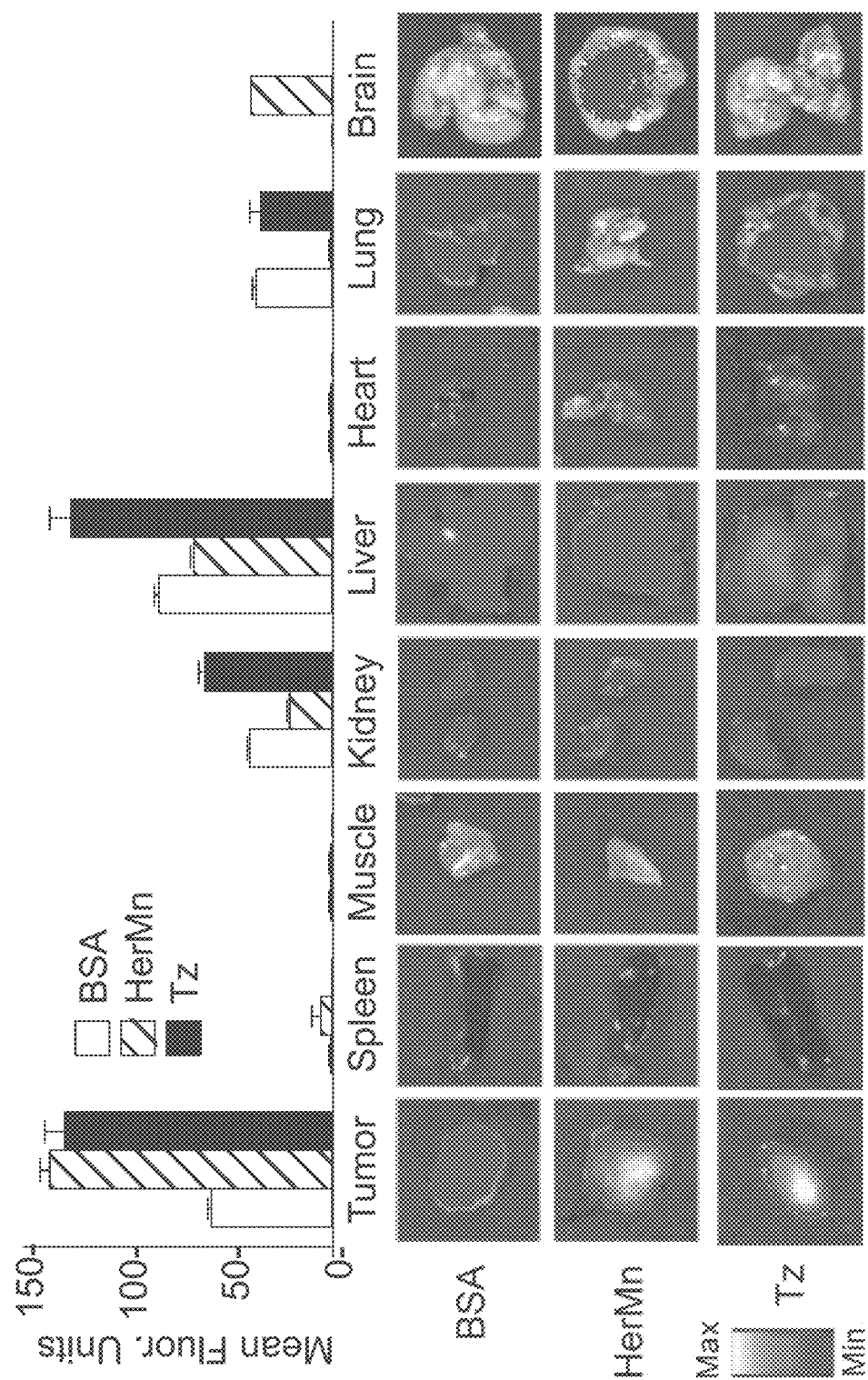
FIG. 17 shows the biodistribution in tumor-bearing mice. Xenogen imaging and quantification of Alexa680-labeled HerMn, trastuzumab (Tz) and BSA (12 nmol ea) after tail vein injection. Graph shows mean fluorescence−/+SEM.
Figure 18A:
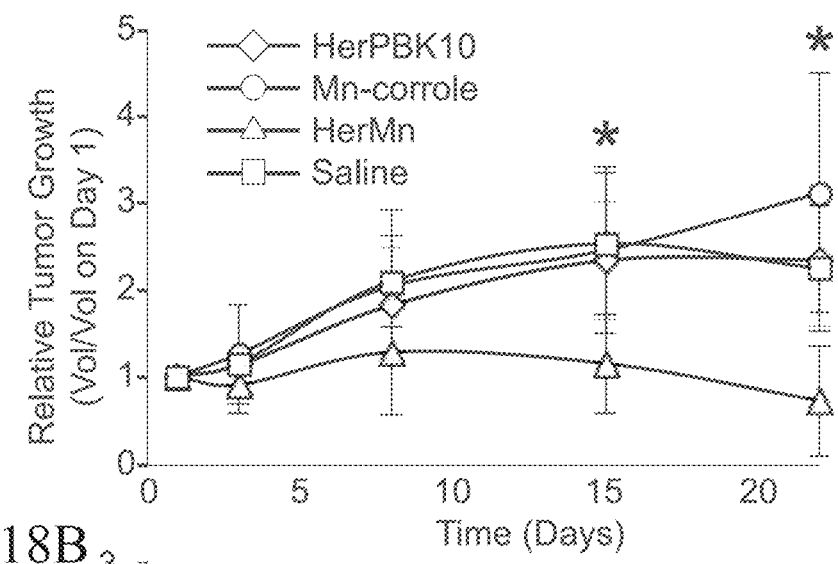
FIGS. 18A-18B show the data for the therapeutic efficacy of HerMn.
Figure 18B:
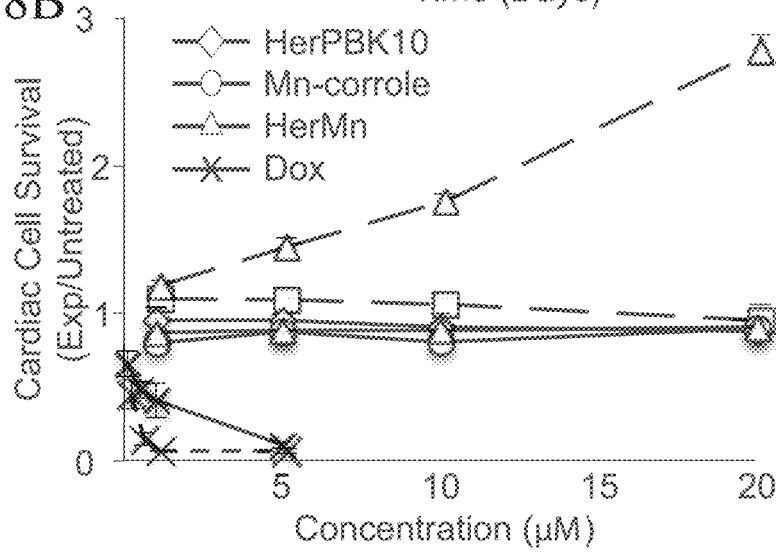
Figure 19:
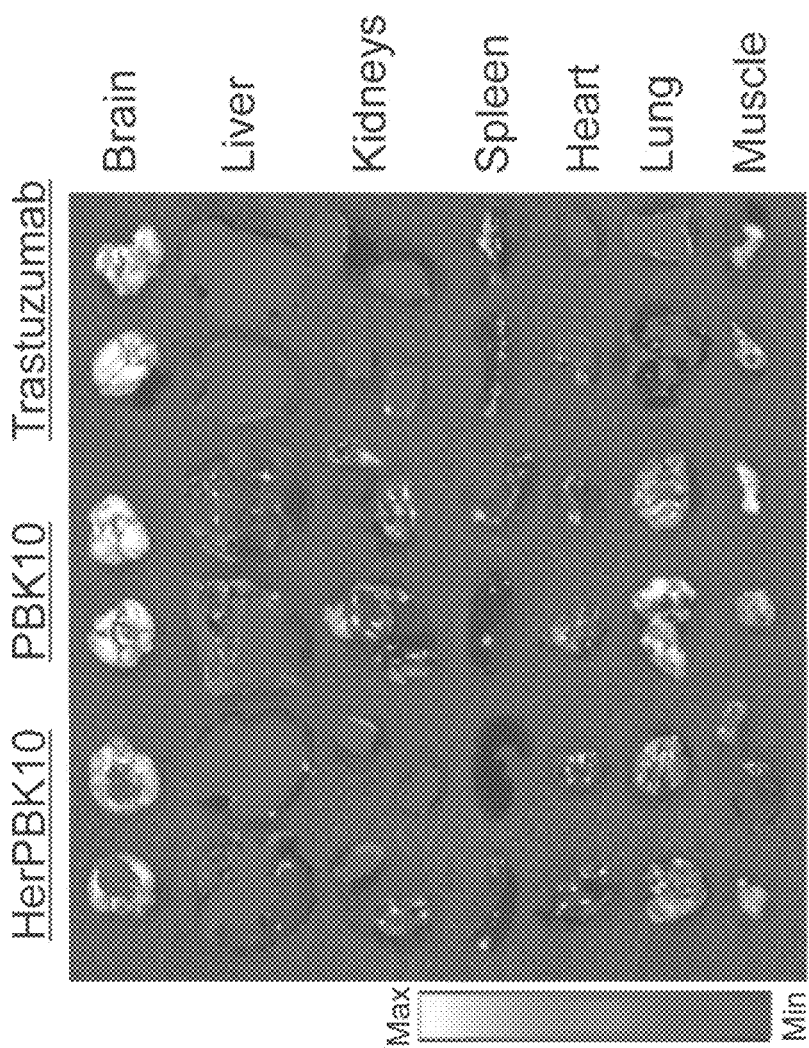
FIG. 19 shows the tissue distribution of HerPBK10 in mice with no tumors.

It has been found that, in addition to accumulating in tumors after systemic delivery in mice, HerMn can distribute to the brain in contrast to trastuzumab (Tz) (FIG. 17). HerPBK10 injected in the tail veins of mice without tumors also show brain localization, whereas systemic delivery of PBK10 (which lacks the HER3 targeting ligand) shows no detectable brain delivery (FIG. 19). It has also been found that HerMn is not only non-toxic to human cardiosphere-derived cells (CDCs), but at escalating doses with extended exposure, augments CDC survival in culture, in contrast to doxorubicin (which has known cardiotoxicity), and Her-PBK10 alone, which has no toxic or growth promoting effect on tumor cells or CDCs (FIG. 18B). This supports previous findings in a model of optic neuropathy in vitro and in vivo, showing that the Mn-corrole can be neuroprotective. This appears to be unique to the Mn-corrole, as the Ga-corrole showed no such neuroprotective effect.

Together, these findings indicate that HerMn imparts a beneficial effect on normal tissue while targeting toxicity to tumor tissue, especially brain metastases with elevated HER3. The targeting specificity of HerMn renders this point less relevant, as a minority of systemic particles appear to distribute to non-tumor tissue (FIG. 17). But, as relatively low corrole levels afford neuroprotection, as well as tumor toxicity (FIG. 18A), this potential dual activity is worth exploring.

Applications

HerMn has the capability of delivering toxicity to brain-metastatic breast tumors while sparing off-target tissue due to both its targeting capacity and ability to provide protection to normal tissue such as the brain and heart.

Example 5: Targeting Beta-1 Integrins Using *Yersinia enterocolitica* Invasin-Derived Peptide

*Yersinia enterocolitica* is a bacterial pathogen that invades the intestinal epithelium, particularly the Peyer's patches of the intestinal wall, and causes food poisoning. Binding and entry of intestinal epithelia occurs through the interaction of the bacterial invasin (Inv) protein with beta-1 integrins, which are predominantly expressed on epithelial cells overlying Peyer's patches.

The plasmid containing the nucleotide sequence encoding Invasin (pHIT123-Inv) was used as a PCR template, and oligonucleotide primers were designed to amplify the minimal sequence encoding the beta-1 integrin binding site (~600 bp) while introducing restriction sites for in-frame cloning into exogenous peptides for targeted delivery. The primers used included the following sequences: 5'-ACAGAGCTCATAACCGGCATTAACGTGAAT-3' (SEQ ID NO:6); 5'-CTGTGTGCGGAGCCGCAATAG-GAATTCATC-3' (SEQ ID NO:7); and 5'-GATGAATTCC-TATTGCGGCTCCGCACACAG-3' (SEQ ID NO:8). These primers are used for amplifying and adding SacI and EcoRI restriction sites to Inv insert. Additional primers included the following sequences: 5'-GTCCAAAAC-CAAGAAAAGGCGGAGCAGCTGTAC-3' (SEQ ID NO:9); 5'-ACAATGACGCGTGTA-CAGCTGCTCCGCCTTTTCTTGGTTTTGGAC-3' (SEQ ID NO:10); 5'-CCGCTGTGTGCGGAGCCGCAAGGAG-GAACGCGTACACAC-3' (SEQ ID NO:11); 5'-GTGTGTACGCGTTCCTCCTTGCGGCTCCGCACAC AGCGG-3' (SEQ ID NO:12); and 5'-ACACACG-GATCCTTGCGGCTCCGCACACAGCGG-3' (SEQ ID NO:13). These primers introduce MluI or BamHI restriction sites for cloning into either Knob or full-length fiber constructs.

The exogenous peptides encode the adenovirus (Ad) capsid fiber and knob proteins. The fiber delineates each of the antenna-like projections extending from the Ad capsid that mediate primary cell binding to initiate infection, and are comprised of an N-terminal long fibrous shaft domain followed by a C-terminal globular knob domain. The knob domain is what specifically interacts with cell surface receptor and is produced as a soluble protein in the absence of the shaft. Inv is an effective ligand when fused to PBK10.

The Inv sequence is inserted into the knob using two strategies of replacing knob sub-domains with Inv, resulting in the recombinant knob constructs, ABCJ-Inv and AGJ-Inv. Recombinant protein is produced in bacteria from pRSET vectors expressing these constructs, as both N-terminally GFP-tagged (GFP-ABCJ-Inv and GFP-AGJ-Inv) and untagged protein. In a third strategy, Inv was inserted into the DG loop of the knob and used in vitro translation to produce S35-labeled protein. Native gel electrophoresis showed the recombinant protein maintained the formation of oligomers (dimers and trimers) similar to wild-type soluble knob (thus suggesting that the Inv insert does not confound the tertiary structure of the fusion protein). In all scenarios, a full-length soluble protein is produced.

Constructs in which Inv replaced the knob of the full-length fiber protein were also created. A baculovirus vector was used to express the protein in bacteria. A second fiber construct was created to express Inv in between the shaft and knob domains of the full-length fiber protein, with a FactorX cleavage site introduced between Inv and Knob.

Example 6: Ligand for CD4

The amino acid sequence, TITLPCRIKQFINMWQEVGKAMYAPPIS-GQIRCSSNITGLLLTR (SEQ ID NO:5), derived from the CD4 binding domain of the human immunodeficiency virus (HIV) gp120 envelope protein, is sufficient for binding to CD4. This sequence was obtained using standard molecular biology techniques. The nucleic acid sequence encoding SEQ ID NO:5 (~132 nt) was cloned into pBluescript (PSK) plasmid. Ethidium bromide stained electrophoresis gel showed excision of insert (~132 nt) from the vector (~3 kb) by BamHI-EcoRI digest. The resulting product is then inserted in-frame with exogenous peptides such as PBK10 for targeting such delivery proteins to cells expressing CD4 (i.e. "helper" T-cells).

What is claimed is:

1. A drug delivery molecule, comprising:
   a polypeptide comprising a penton base segment that penetrates a membrane and a payload binding domain; and
   a mRNA molecule complexed with the polypeptide, wherein the mRNA molecule encodes a protein that can be expressed upon entry into a cell.

2. The drug delivery molecule of claim 1, wherein the polypeptide further comprises a ligand that targets a cell surface molecule.

3. The drug delivery molecule of claim 2, wherein the cell surface molecule is a receptor.

4. The drug delivery molecule of claim 2, wherein the cell surface molecule is HER3.

5. The drug delivery molecule of claim 2, wherein the ligand is derived from heregulin-α.

6. The drug delivery molecule of claim 2, wherein the ligand comprises an Ig-like domain and an EGF-like domain of heregulin-α.

7. The drug delivery molecule of claim 1, wherein the payload binding domain comprises a decalysine motif.

8. The drug delivery molecule of claim 1, wherein the mRNA binds to the payload binding domain through electrostatic interactions.

9. The drug delivery molecule of claim 1, wherein the penton base segment is an adenovirus penton base protein or a fragment thereof.

10. The drug delivery molecule of claim 1, wherein the drug delivery polypeptide is HerPBK10.

* * * * *

SEQUENCE LISTING

```
<160> NUMBER OF SEQ ID NOS: 14

<210> SEQ ID NO 1
<211> LENGTH: 24
<212> TYPE: DNA
<213> ORGANISM: Homo sapiens

<400> SEQUENCE: 1
agtgagctcg agactatcac tgtg                                              24

<210> SEQ ID NO 2
<211> LENGTH: 51
<212> TYPE: DNA
<213> ORGANISM: Homo sapiens

<400> SEQUENCE: 2
gttggtgact ttctcccacc ttcaccacct tcatctagat atccatggta t               51

<210> SEQ ID NO 3
<211> LENGTH: 6
<212> TYPE: PRT
<213> ORGANISM: Artificial Sequence
<220> FEATURE:
<223> OTHER INFORMATION: Synthesized sequence

<400> SEQUENCE: 3

Gly Gly Ser Gly Gly Ser
1               5

<210> SEQ ID NO 4
<211> LENGTH: 30
<212> TYPE: DNA
<213> ORGANISM: Homo sapiens

<400> SEQUENCE: 4
cgcctgagca acgcggcggg catccgcaag                                        30

<210> SEQ ID NO 5
<211> LENGTH: 44
<212> TYPE: PRT
<213> ORGANISM: Human immunodeficiency virus

<400> SEQUENCE: 5

Thr Ile Thr Leu Pro Cys Arg Ile Lys Gln Phe Ile Asn Met Trp Gln
1               5                   10                  15

Glu Val Gly Lys Ala Met Tyr Ala Pro Pro Ile Ser Gly Gln Ile Arg
            20                  25                  30

Cys Ser Ser Asn Ile Thr Gly Leu Leu Leu Thr Arg
        35                  40

<210> SEQ ID NO 6
<211> LENGTH: 30
<212> TYPE: DNA
<213> ORGANISM: Yersinia enterocolitica

<400> SEQUENCE: 6
acagagctca taaccggcat taacgtgaat                                        30
```

<210> SEQ ID NO 7
<211> LENGTH: 30
<212> TYPE: DNA
<213> ORGANISM: Yersinia enterocolitica

<400> SEQUENCE: 7
ctgtgtgcgg agccgcaata ggaattcatc 30

<210> SEQ ID NO 8
<211> LENGTH: 30
<212> TYPE: DNA
<213> ORGANISM: Yersinia enterocolitica

<400> SEQUENCE: 8
gatgaattcc tattgcggct ccgcacacag 30

<210> SEQ ID NO 9
<211> LENGTH: 33
<212> TYPE: DNA
<213> ORGANISM: Yersinia enterocolitica

<400> SEQUENCE: 9
gtccaaaacc aagaaaaggc ggagcagctg tac 33

<210> SEQ ID NO 10
<211> LENGTH: 45
<212> TYPE: DNA
<213> ORGANISM: Yersinia enterocolitica

<400> SEQUENCE: 10
acaatgacgc gtgtacagct gctccgcctt ttcttggttt tggac 45

<210> SEQ ID NO 11
<211> LENGTH: 39
<212> TYPE: DNA
<213> ORGANISM: Yersinia enterocolitica

<400> SEQUENCE: 11
ccgctgtgtg cggagccgca aggaggaacg cgtacacac 39

<210> SEQ ID NO 12
<211> LENGTH: 39
<212> TYPE: DNA
<213> ORGANISM: Yersinia enterocolitica

<400> SEQUENCE: 12
gtgtgtacgc gttcctcctt gcggctccgc acacagcgg 39

<210> SEQ ID NO 13
<211> LENGTH: 33
<212> TYPE: DNA
<213> ORGANISM: Yersinia enterocolitica

<400> SEQUENCE: 13
acacacggat ccttgcggct ccgcacacag cgg 33

<210> SEQ ID NO 14
<211> LENGTH: 220
<212> TYPE: PRT
<213> ORGANISM: Homo sapiens

<400> SEQUENCE: 14

Ser Glu Val Gly Asn Ser Gln Ala Val Cys Pro Gly Thr Leu Asn Gly
1 5 10 15

-continued

```
Leu Ser Val Thr Gly Asp Ala Glu Asn Gln Tyr Gln Thr Leu Tyr Lys
             20                  25                  30

Leu Tyr Glu Arg Cys Glu Val Val Met Gly Asn Leu Glu Ile Val Leu
         35                  40                  45

Thr Gly His Asn Ala Asp Leu Ser Phe Leu Gln Trp Ile Arg Glu Val
     50                  55                  60

Thr Gly Tyr Val Leu Val Ala Met Asn Glu Phe Ser Thr Leu Pro Leu
 65              70                  75                  80

Pro Asn Leu Arg Val Val Arg Gly Thr Gln Val Tyr Asp Gly Lys Phe
             85                  90                  95

Ala Ile Phe Val Met Leu Asn Tyr Asn Thr Asn Ser Ser His Ala Leu
             100                 105                 110

Arg Gln Leu Arg Leu Thr Gln Leu Thr Glu Ile Leu Ser Gly Gly Val
         115                 120                 125

Tyr Ile Glu Lys Asn Asp Lys Leu Cys His Met Asp Thr Ile Asp Trp
     130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
             165                 170                 175

Gly Pro Gly Ser Glu Asp Cys Gln Thr Leu Thr Lys Thr Ile Cys Ala
             180                 185                 190

Pro Gln Cys Asn Gly His Cys Phe Gly Pro Asn Pro Asn Gln Cys Cys
         195                 200                 205

His Asp Glu Cys Ala Gly Gly Cys Ser Gly Pro Gln
     210                 215                 220
```